(12) United States Patent
Kozikowski et al.

(10) Patent No.: US 6,610,743 B2
(45) Date of Patent: Aug. 26, 2003

(54) BICYCLIC METABOTROPIC GLUTAMATE RECEPTOR LIGANDS

(75) Inventors: Alan P. Kozikowski, Princeton, NJ (US); Darryl Hugh Steensma, New York, NY (US); Werner Tueckmantel, Washington, DC (US); Gian Luca Araldi, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 10/092,388

(22) Filed: Mar. 6, 2002

(65) Prior Publication Data

US 2002/0165200 A1 Nov. 7, 2002

Related U.S. Application Data

(63) Continuation of application No. 09/769,737, filed on Jan. 25, 2001, now Pat. No. 6,376,532, which is a continuation of application No. 09/118,042, filed on Jul. 17, 1998, now Pat. No. 6,204,292.

(60) Provisional application No. 60/052,972, filed on Jul. 18, 1997, and provisional application No. 60/064,304, filed on Nov. 5, 1997.

(51) Int. Cl.[7] .................. A61K 31/196; C07C 61/12
(52) U.S. Cl. .................. 514/561; 562/500; 562/502; 562/507; 562/509; 562/7; 562/11; 560/118; 548/253; 548/259; 514/381; 514/529; 514/557; 514/579

(58) Field of Search ................... 514/561, 574, 514/557, 529, 381; 562/500, 502, 507, 509, 7, 11; 560/118; 548/253, 254

(56) References Cited

PUBLICATIONS

Baker, S. R. et al.: The synthesis of [2.2.1]bicyclooctane and [3.1.1]bicycloheptane based amino acids as constrained glutamate analogues. tetrahed. lett. vol. 40, pp. 781–784, 1999.*

Porter et al.; "Growth Inhibition by Methionine Analog Inhibitors of S–Adenosylmethionine Biosynthesis in the Absence of Polyamine Depletion", Biochemical and Biophysical Research communications, 122(1): 350–357, (Jul. 18, 1994).

Tellier, F. et al.; "Synthesis of Conformationally–Contrained Stereospecific Analogs of Glutamic Acid as Antagonists of Metabotropic Receptors", Bioorg. Med. Chem. Lett., 5: 2627–2632, (1995).

* cited by examiner

*Primary Examiner*—Charanjit S. Aulakh
(74) *Attorney, Agent, or Firm*—Dana M. Gordon; Foley Hoag LLP

(57) ABSTRACT

The present invention provides bicyclic metabotropic glutamate receptor ligands, as well as compositions comprising such ligands, and and methods for their use.

15 Claims, 16 Drawing Sheets

| | | EC$_{50}$ values (μm) | |
|---|---|---|---|
| | | Group I mGluRs | |
| | | mGluR1a | mGluR5a |
| | Glu | 4.9 ± 0.21 | 3.1 ± 0.23 |
| | ACPD | 15 ± 2.2 | 23 ± 2.6 |
| | AP4 | NE | NE |
| BcACPD | DHS-4-79 | 8.4 ± 0.88 | 5.5 ± 0.73 |
| | 6c | 121 ± 10 | 57 ± 6 |
| | 6d | >1000 | >1000 |
| | 6a | 232 ± 23 | ·91 ± 11 |
| | 6b | 1.6 ± 0.14 | 0.72 ± 0.11 |

| | | Group II mGluRs | |
|---|---|---|---|
| | | mGluR2 | mGluR3/1a |
| | Glu | 0.29 ± 0.07 | 1.9 ± 0.31 |
| | ACPD | 2.0 ± 0.3 | 40 ± 5.8 |
| | AP4 | NE | NE |
| BcACPD | DHS-4-79 | 1.2 ± 0.14 | 13 ± 1.8 |
| | 6c | 54 ± 9 | 185 ± 87 |
| | 6d | >1000 | >1000 |
| | 6a | 38 ± 10 | 255 ± 84 |
| | 6b | 0.33 ± 0.06 | 2.2 ± 1.5 |

| | | Group III mGluRs | |
|---|---|---|---|
| | | mGluR4a | mGluR6 |
| | Glu | 9.8 ± 0.81 | 4.9 ± 0.37 |
| | ACPD | ~ 800 | 82 ± 6.2 |
| | AP4 | 0.33 ± 0.087 | 0.28 ± 0.025 |
| BcACPD | DHS-4-79 | 82 ± 8.6 | 29 ± 16 |
| | 6c | ~1000 | ~ 800 |
| | 6d | >1000 | >1000 |
| | 6a | >1000 | >1000 |
| | 6b | 23 ± 7.1 | 5.3 ± 0.93 |

Fig. 5

BICYCLIC METABOTROPIC GLUTAMATE RECEPTOR LIGANDS

PRIORITY OF INVENTION

This application is a continuation of U.S. patent application Ser. No. 09/769,737, filed Jan. 25, 2001 now U.S. Pat. No. 6,376,532; which is a continuation of U.S. patent application Ser. No. 09/118,042, filed Jul. 17, 1998 now U.S. Pat. No. 6,204,292; which claims priority to U.S. Provisional Application serial No. 60/052,972, filed Jul. 18, 1997, and U.S. Provisional Application serial No. 60/064,304, filed Nov. 5, 1997.

BACKGROUND OF THE INVENTION

L-Glutamate, which is the most abundant neurotransmitter in the CNS, mediates the major excitatory pathway in mammals, and thus is referred to as an excitatory amino acid (EAA). The receptors that respond to glutamate are called EAA receptors. The EAA receptors are of great physiological importance playing a role in a variety of physiological processes, such as long-term potentiation (learning and memory), the development of synaptic plasticity, motor control, respiration, cardiovascular regulation, emotional states and sensory perception.

The excessive or inappropriate stimulation of EAA receptors leads to neuronal cell damage or loss by way of a mechanism known as excitotoxicity. The medical consequence of such neuronal degeneration makes the abatement of these degenerative neurological processes an important therapeutical goal.

EAA receptors are classified into two general types. Receptors that are directly coupled to the opening of cation channels in the cell membranes of the neuron are termed "ionotropic". The second type of receptor is the G-protein or second messenger-linked "metabotropic" EAA receptor. This second type is coupled to multiple second messenger systems that lead to enhanced phosphoinositide hydrolysis, activation of phospholipase D, increases or decreases in cAMP formation, and changes in ion channel function. The metabotropic glutamate receptors (mGluR) have been distinguished pharmacologically from the ionotropic glutamate receptors by the use of the metabotropic glutamate-selective antagonist (1S,3R)-1-aminocyclopentane-1,3-dicarboxylic acid, generally through measurements involving phosphoinositide hydrolysis or $Ca^{2+}$ mobilization. To date the use of expression cloning techniques has led to the identification of eight mGluR subtypes, which have been placed into three major categories (Groups) based on their molecular structure, signal transduction mechanisms, and pharmacological properties. Group I mGluRs (mGluR1 and 5) are coupled to phosphoinositide (PI) hydrolysis, whereas Group II (mGluR2 and 3) and Group III (mGluR4, 6, 7, and 8) are negatively linked to adenylyl cyclase activity.

Glutamate receptors play a role in numerous neurological, neurodegenerative, psychiatric, and psychological disorders, and a variety of mammalian disease states are associated with "abnormal activity" of these receptors. As used herein, the term "abnormal activaty" includes either an increase or a decrease in activation of the receptors as compared to normal function in said mammal. For example, metabotropic glutamate receptor ligands should be useful in the treatment of diseases or conditions including epilepsy, cerebral ischemia, pain, anxiety, spinal cord injury, chronic neurodegenerative diseases (e.g. Alzheimer's disease), Lou Gherig's disease (ALS), Parkinson's disease, Multiple Sclerosis and other diseases or conditions that result in progressive loss of neuronal cells and or cellular function.

In order to better characterize the roles of mGluRs in physiological processes, there is a need to identify novel, high affinity compounds that are mGluR Group or subtype specific. Such compounds are needed for use as pharmacological tools for the further investigation of mGluR function, and should be useful as therapeutic agents for the treatment of diseases or conditions associated with abnormal activity of metabotropic glutamate receptors.

SUMMARY OF THE INVENTION

The present invention provides compounds that are ligands for metabotropic glutamate receptors. Accordingly there is provided a compound of the invention which is a bicyclic compound of formula I:

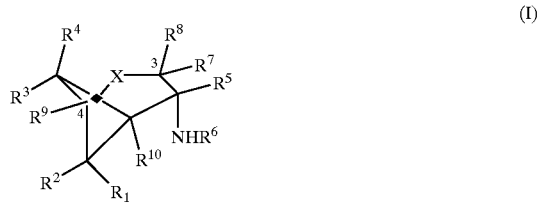

(I)

wherein $R^1$, $R^2$, $R^3$, $R^4$, $R^7$, $R^8$, $R^9$, and $R^{10}$ are each independently hydrogen, carboxy, tetrazolyl, —$SO_2OH$, —$PO(OH)_2$, —$B(OH)_2$, ($C_1$–$C_6$)alkyl, ($C_3$–$C_6$)cycloalkyl, ($C_3$–$C_6$)cycloalkyl($C_1$–$C_6$)alkyl, ($C_2$–$C_6$)alkenyl, ($C_2$–$C_6$)alkynyl, ($C_1$–$C_6$)alkoxy, halo($C_1$–$C_6$)alkyl, hydroxy($C_1$–$C_6$)alkyl, ($C_1$–$C_6$)alkanoyl, ($C_1$–$C_6$)alkanoyloxy, ($C_1$–$C_6$)alkoxycarbonyl, cyano, halo, —$CONR_aR_b$, —$NR_cR_d$—$SR_e$, aryl, heteroaryl, aryl($C_1$–$C_6$)alkyl, diaryl($C_1$–$C_6$)alkyl, or heteroaryl($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$)alkanoyloxy, ($C_1$–$C_6$)alkoxycarbonyl, cyano, nitro, trifluoromethyl, trifluoromethoxy, and carboxy;

$R^5$ is carboxy, tetrazolyl, ($C_1$–$C_6$)alkoxycarbonyl, —$SO_2OH$, —$B(OH)_2$, or —$PO(OH)_2$;

$R^6$ is hydrogen, ($C_1$–$C_6$)alkyl, ($C_3$–$C_6$)cycloalkyl, ($C_3$–$C_6$)cycloalkyl($C_1$–$C_6$)alkyl, aryl, aryl($C_1$–$C_6$)alkyl, heteroaryl, heteroaryl($C_1$–$C_6$)alkyl, ($C_1$–$C_6$)alkoxycarbonyl, or ($C_1$–$C_6$)alkanoyl;

X is absent (a direct or single bond connects $C_3$ and $C_4$), oxy (—O—), thio (—S—), sulfinyl (—SO—), sulfonyl (—$SO_2$—), —$C(R_f)(R_g)$—, seleno (—Se—), —$P(R_x)$—, or —$N(R_x)$—, wherein $R_x$ is hydrogen, ($C_1$–$C_6$)alkyl, ($C_1$–$C_6$)alkanoyl, aryl, aryl($C_1$–$C_6$)alkyl, ($C_1$–$C_6$)alkoxycarbonyl, or aryl($C_1$–$C_6$)alkoxycarbonyl;

each $R_a$ $R_b$ and $R_c$ is independently hydrogen, ($C_1$–$C_6$)alkyl, ($C_3$–$C_6$)cycloalkyl, ($C_2$–$C_6$)alkenyl, ($C_2$–$C_6$)alkynyl, aryl, heteroaryl, benzyl, or phenethyl;

each $R_c$ or $R_d$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

$R_f$ and $R_g$ are each independently hydrogen, carboxy, ($C_1$–$C_6$)alkyl, ($C_3$–$C_6$)cycloalkyl, ($C_3$–$C_6$)cycloalkyl ($C_1$–$C_6$)alkyl, ($C_2$–$C_6$)alkenyl, ($C_2$–$C_6$)alkynyl, ($C_1$–$C_6$)alkoxy, halo($C_1$–$C_6$)alkyl, hydroxy($C_1$–$C_6$) alkyl, ($C_1$–$C_6$)alkanoyl, ($C_1$–$C_6$)alkanoyloxy, ($C_1$–$C_6$) alkoxycarbonyl, cyano, halo, —$CONR_hR_i$, —$NR_jR_k$, —$SR_m$, aryl, heteroaryl, aryl($C_1$–$C_6$)alkyl, or heteroaryl($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3C_6$)cycloalkyl($C_1$–$C_6$)alkyl, ($C_1$–$C_6$)alkanoyl, ($C_1$–$C_6$)alkanoyloxy, ($C_1$–$C_6$)alkoxycarbonyl, cyano, nitro, trifluoromethyl, trifluoromethoxy, and carboxy; or $R_f$ and $R_g$ together are oxo (=O) or thioxo (=S);

each $R_h$, and $R_i$, and $R_m$ is independently hydrogen, ($C_1$–$C_6$)alkyl, ($C_3$–$C_6$)cycloalkyl, ($C_2$–$C_6$)alkenyl, ($C_2$–$C_6$)alkynyl, aryl, heteroaryl, benzyl, or phenethyl; and each $R_j$ or $R_k$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_j$ and $R_k$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

or a pharmaceutically acceptable salt or prodrug thereof; wherein at least one of $R^1$, $R^2$, $R^3$, $R^4$, $R^9$, and $R^{10}$ is carboxy, tetrazolyl, —$SO_2OH$, —$PO(OH)_2$, or —$B(OH)_2$.

The invention also provides a pharmaceutical composition comprising a compound of formula I, or a pharmaceutically acceptable salt or prodrug thereof, in combination with a pharmaceutically acceptable diluent or carrier.

Additionally, the invention provides a therapeutic method for preventing or treating a pathological condition or symptom in a mammal, such as a human, which is associated with abnormal activity of metabotropic glutamate receptors, comprising administering to a mammal in need of such therapy, an effective amount of a compound of formula I, or a pharmaceutically acceptable salt or prodrug thereof.

The invention provides a compound of formula I for use in medical diagnosis or therapy (preferably for use in treating a pathological condition or symptom in a mammal, such as a human, associated with abnormal activity of metabotropic glutamate receptors), as well as the use of a compound of formula I for the manufacture of a medicament for the treatment of a pathological condition or symptom in a mammal, such as a human, which is associated with abnormal activity of metabotropic glutamate receptors.

The invention provides a method for binding a compound of formula I to metabotropic glutamate receptors comprising contacting mammalian tissue comprising said receptors, in vivo or in vitro, with an amount of a compound of formula I effective to bind to said receptors. Tissue comprising ligand bound metabotropic glutamate receptors can be used to measure the selectivity of test compounds for specific mGluR Groups or subtypes, or can be used as a tool to identify potential therapeutic agents for the treatment of diseases or conditions associated with abnormal activation of metabotropic glutamate receptors, by contacting said agents with said ligand-receptor complexes, and measuring the extent of displacement of the ligand and/or binding of the agent.

The invention also provides compounds of formula I comprising a label (e.g a detectable radionuclide such as $^3H$, $^{11}C$, $^{14}C$, or $^{13}N$, or a detectable nonradioactive nuclide such as $^2H$, $^{13}C$, $^{15}N$, or $^{18}O$), and their use e.g. in stuties of receptor function or in the elucidation of the structure, function or mechanism of competitive ligand interaction. Techniques and radionuclides suitable for labeling compounds for in vivo or in vitro detection are well known to the art.

BRIEF DESCRIPTION OF THE FIGURES

FIG. 5 Shows biological data for compounds of the invention.

DETAILED DESCRIPTION

Figure 1:
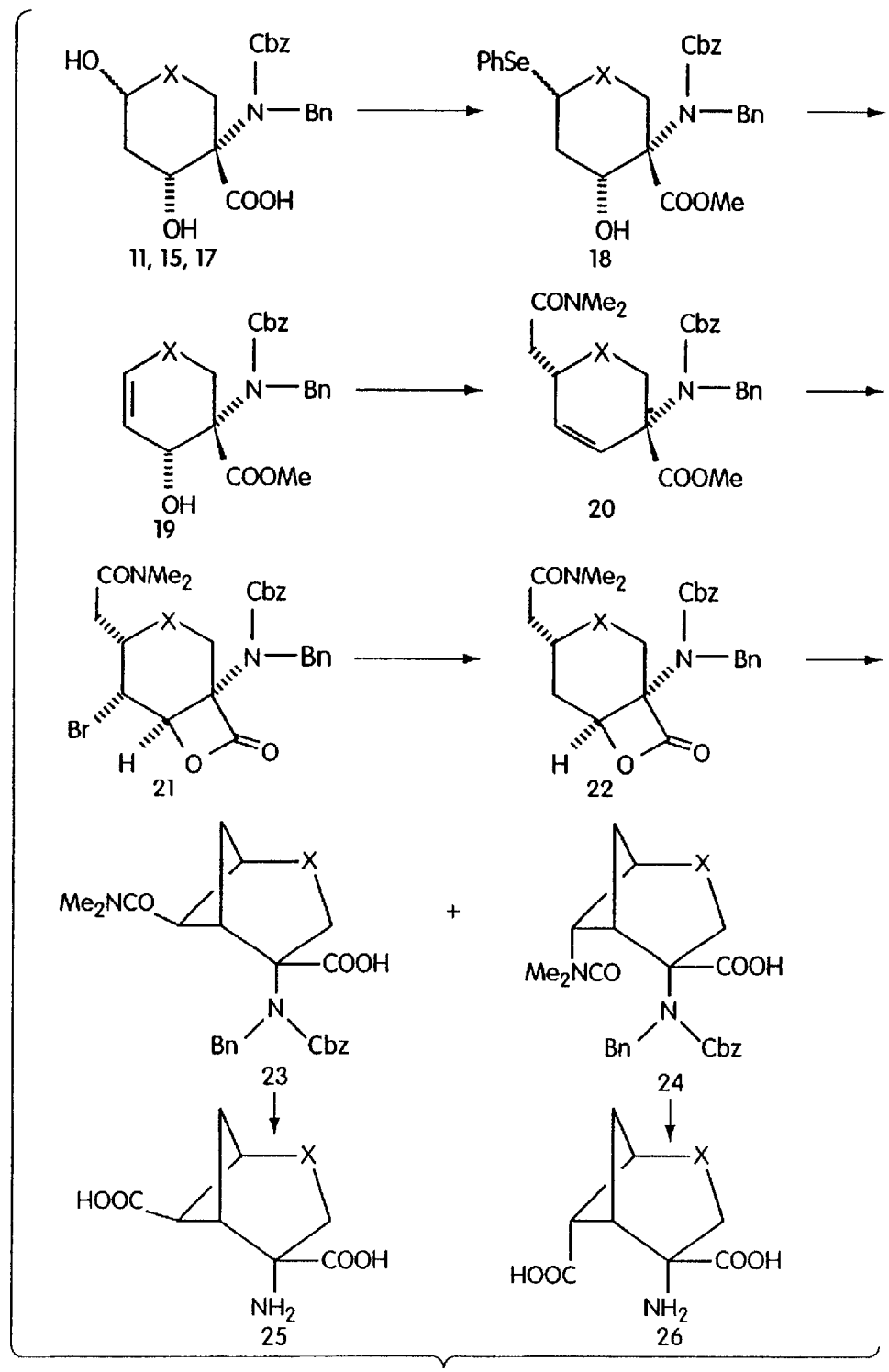
FIG. 1 Illustrates the synthesis of compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, OH, ($C_1$–$C_4$) alkyl, ($C_1$–$C_4$)alkoxy, phenyl or benzyl, as well as a radical of an ortho-fused bicyclic heterocycle of about eight to ten ring atoms derived therefrom, particularly a benz-derivative or one derived by fusing a propylene, trimethylene, or tetrarethylene diradical thereto.

It will be appreciated by those skilled in the art that compounds of the invention having a chiral center may exist in and be isolated in optically active and racemic forms.

Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine metabotropic glutamate receptor agonist activity using the standard tests described herein, or using other similar tests which are well known in the art.

Specific and preferred values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_2-C_6)$alkenyl can be vinyl, allyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl 3-hexynyl, 4-hexynyl, or 5-hexynyl; $(C_1-C_6)$alkanoyl can be acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_1-C_6)$alkanoyloxy can be formyloxy, acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), indolyl, isoquinolyl (or its N-oxide) or quinolyl (or its N-oxide).

A specific value for $R^1$ is hydrogen.

A specific value for $R^2$ is carboxy.

A specific value for $R^3$ is hydrogen.

A specific value for $R^4$ is carboxy or hydroxymethyl.

A specific value for $R^5$ is carboxy.

A specific value for $R^6$ is hydrogen

Specifically, $R^7$, and $R^8$ are each hydrogen.

Specifically, $R^9$, and $R^{10}$ are each hydrogen.

Specifically, X can be absent. Another specific value for X is oxy, thio, sulfinyl, sulfonyl, or —N($R_x$)—, wherein $R_x$ is hydrogen, $(C_1-C_6)$alkyl, $(C_1-C_6)$alkanoyl, phenyl, benzyl, or benzyloxycarbonyl. Yet another specific value for X is methylene (—CH$_2$—).

A specific value for each of $R_f$ and $R_g$ is hydrogen.

A specific compound is a compound of formula II:

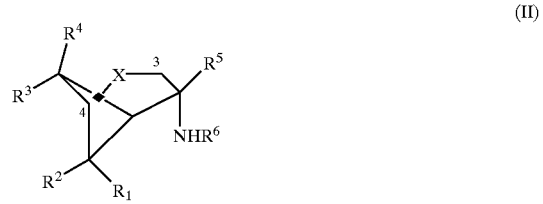

(II)

wherein
  $R^1$, $R^2$, $R^3$, and $R^4$, are each independently hydrogen, carboxy, tetrazolyl, —SO$_2$OH, —PO(OH)$_2$, $(C_1-C_6)$alkyl, $(C_3-C_6)$cycloalkyl, $(C_3-C_6)$cycloalkyl$(C_1-C_6)$alkyl, $(C_2-C_6)$alkenyl, $(C_2-C_6)$alkynyl, $(C_1-C_6)$alkoxy, halo$(C_1-C_6)$alkyl, hydroxy$(C_1-C_6)$alkyl, $(C_1-C_6)$alkanoyl, $(C_2-C_6)$ alkanoyloxy, $(C_1-C_6)$alkoxycarbonyl, cyano, halo, —CONR$_a$R$_b$, —NR$_c$R$_d$, —SR$_e$, aryl, heteroaryl, aryl$(C_1-C_6)$alkyl, or heteroaryl$(C_1-C_6)$alkyl, wherein any aryl or heteroaryl may optionally be substituted with 1, 2 or 3 substituents selected from the group consisting of halo, hydroxy, $(C_1-C_6)$alkoxy, $(C_1-C_6)$alkyl, $(C_3-C_6)$cycloalkyl, $(C_3-C_6)$cycloalkyl$(C_1-C_6)$alkyl, $(C_1-C_6)$alkanoyl, $(C_1-C_6)$alkanoyloxy, $(C_1-C_6)$alkoxycarbonyl, cyano, nitro, trifluoromethyl, trifluoromethoxy, and carboxy;

$R^5$ is carboxy, tetrazolyl, $(C_1-C_6)$alkoxycarbonyl, —SO$_2$OH or —PO(OH)$_2$;

$R^6$ is hydrogen, $(C_1-C_6)$alkyl, $(C_3-C_6)$cycloalkyl, $(C_3-C_6)$cycloalkyl$(C_1-C_6)$alkyl, phenyl, benzyl, $(C_1-C_6)$alkoxycarbonyl, $(C_1-C_6)$alkanoyl, or phenethyl;

X is absent, oxy (—O—), thio (—S—), sulfinyl (—SO—), sulfonyl (—SO$_2$—), —C(R$_f$)(R$_g$)—, or —N(R$_x$)—, wherein R$_x$ is hydrogen, $(C_1-C_6)$alkyl, $(C_1-C_6)$alkanoyl, phenyl, benzyl, or benzyloxycarbonyl;

each R$_a$ R$_b$ and R$_e$ is independently hydrogen, $(C_1-C_6)$alkyl, $(C_3-C_6)$cycloalkyl, $(C_2-C_6)$alkenyl, $(C_2-C_6)$alkynyl, aryl, heteroaryl, benzyl, or phenethyl;

each R$_c$ or R$_d$ is independently hydrogen, $(C_1-C_6)$alkyl, $(C_3-C_6)$cycloalkyl, $(C_2-C_6)$alkenyl, $(C_2-C_6)$alkynyl, $(C_1-C_6)$alkanoyl, aryl, heteroaryl, benzyl, or phenethyl; or R$_c$ and R$_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

R$_f$ and R$_g$ are each independently hydrogen, carboxy, $(C_1-C_6)$alkyl, $(C_3-C_6)$cycloalkyl, $(C_3-C_6)$cycloalkyl$(C_1-C_6)$alkyl, $(C_2-C_6)$alkenyl, $(C_2-C_6)$alkynyl, $(C_1-C_6)$alkoxy, halo$(C_1-C_6)$alkyl, hydroxy$(C_1-C_6)$alkyl, $(C_1-C_6)$alkanoyl, $(C_2-C_6)$alkanoyloxy, $(C_1-C_6)$alkoxycarbonyl, cyano, halo, —CONR$_h$R$_i$, —NR$_j$R$_k$, or —SR$_m$, aryl, heteroaryl, aryl$(C_1-C_6)$alkyl, or heteroaryl$(C_1-C_6)$alkyl, wherein any aryl or heteroaryl may optionally be substituted with 1, 2 or 3 substituents selected from the group consisting of halo, hydroxy, $(C_1-C_6)$alkoxy, $(C_1-C_6)$alkyl, $(C_3-C_6)$cycloalkyl, $(C_3-C_6)$cycloalkyl$(C_1-C_6)$alkyl, $(C_1-C_6)$alkanoyl, ($C_1$–$C_6$)alkanoyloxy, ($C_1$–$C_6$)alkoxycarbonyl, cyano, nitro, trifluoromethyl, trifluoromethoxy, and carboxy; or $R_f$ and $R_g$ together are oxo (=O) or thioxo (=S); each $R_h$, $R_i$, and $R_m$ is independently hydrogen, ($C_1$–$C_6$) alkyl, ($C_3$–$C_6$)cycloalkyl, ($C_2$–$C_6$)alkenyl, ($C_2$–$C_6$) alkynyl, aryl, heteroaryl, benzyl, or phenethyl; and each $R_j$ or $R_k$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_j$ and $R_k$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

or a pharmaceutically acceptable salt thereof.

A specific group of compounds are compounds of formula I or II wherein at least one of $R^1$, $R^2$, $R^3$, and $R^4$ is carboxy, tetrazolyl, or —$SO_2OH$.

A specific group of compounds are compounds of formula I or II wherein $R^2$ and $R^5$ are carboxy, and $R^1$ is hydrogen.

A specific group of compounds are compounds of formula I or II wherein $R^2$ is carboxy and $R^1$, $R^3$, and $R^4$ are hydrogen.

A specific group of compounds are compounds of formula I or II wherein $R^7$ or $R^8$ is hydrogen, and the other of $R^7$ and $R^8$ is other than hydrogen.

A preferred compound is a compound of formula (I) wherein $R^1$, $R^2$, $R^3$, $R^4$, $R^7$, $R^8$, $R^9$, and $R^{10}$ are each independently hydrogen, carboxy, tetrazolyl, —$SO_2OH$, —$PO(OH)_2$, ($C_1$–$C_6$)alkyl, ($C_3$–$C_6$)cycloalkyl, ($C_3$–$C_6$) cycloalkyl($C_1$–$C_6$)alkyl, ($C_2$–$C_6$)alkenyl, ($C_2$–$C_6$)alkynyl, ($C_1$–$C_6$)alkoxy, halo($C_1$–$C_6$)alkyl, hydroxy($C_1$–$C_6$)alkyl, ($C_1$–$C_6$)alkanoyl, ($C_1$–$C_6$)alkanoyloxy, ($C_1$–$C_6$) alkoxycarbonyl, cyano, halo, —$CONR_aR_b$, —$NR_cR_d$, —$SR_e$, aryl, heteroaryl, aryl($C_1$–$C_6$)alkyl, diaryl($C_1$–$C_6$) alkyl, or heteroaryl($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$) alkanoyloxy, ($C_1$–$C_6$)alkoxycarbonyl, cyano, nitro, trifluoromethyl, trifluoromethoxy, and carboxy; $R^5$ is carboxy, tetrazolyl, ($C_1$–$C_6$)alkoxycarbonyl, —$SO_2OH$, or —$PO(OH)_2$; $R^6$ is hydrogen, ($C_1$–$C_6$)alkyl, ($C_3$–$C_6$) cycloalkyl, ($C_3$–$C_6$)cycloalkyl($C_1$–$C_6$)alkyl, phenyl, benzyl, ($C_1$–$C_6$)alkoxycarbonyl, ($C_1$–$C_6$)alkanoyl, or phenethyl; and X is absent (a direct or single bond connects $C_3$ and $C_4$), oxy (—O—), thio (—S—), sulfinyl (—SO—), sulfonyl (—$SO_2$—), —C($R_f$)($R_g$)—, or —N($R_x$)—, wherein $R_x$ is hydrogen, ($C_1$–$C_6$)alkyl,($C_1$–$C_6$)alkanoyl, phenyl, benzyl, or benzyloxycarbonyl; or a pharmaceutically acceptable salt thereof; wherein at least one of $R^1$, $R^2$, $R^3$, $R^4$, $R^6$, and $R^{10}$ is carboxy, tetrazolyl, —$SO_2OH$, or —$PO(OH)_2$.

A preferred compound is a compound of formula I wherein $R^7$ and $R^8$ are each hydrogen.

A preferred compound is a compound of formula II wherein $R^1$, $R^2$, $R^3$, and $R^4$, are each independently hydrogen, carboxy, tetrazolyl, —$SO_2OH$, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkoxy, halo($C_1$–$C_6$)alkyl, hydroxy($C_1$–$C_6$)alkyl, ($C_1$–$C_6$)alkanoyl, ($C_1$–$C_6$)alkoxycarbonyl, phenyl, benzyl, benzyloxy, phenethyl, cyano, mercapto, ($C_1$–$C_6$)aklylthio, or halo; $R^5$ is carboxy, tetrazolyl, ($C_1$–$C_6$)alkoxycarbonyl, or —$SO_2OH$; and $R^6$ is hydrogen, ($C_1$–$C_6$)alkyl, ($C_3$–$C_6$) cycloalkyl, ($C_3$–$C_6$)cycloalkyl($C_1$–$C_6$)alkyl, phenyl, benzyl, ($C_1$–$C_6$)alkoxycarbonyl, ($C_1$–$C_6$)alkanoyl, or phenethyl; and X is absent; or a pharmaceutically acceptable salt thereof.

A preferred compound is a compound of formula I or II wherein $R^2$ and $R^5$ are carboxy and X is absent.

A preferred compound of the invention is a compound of formula III:

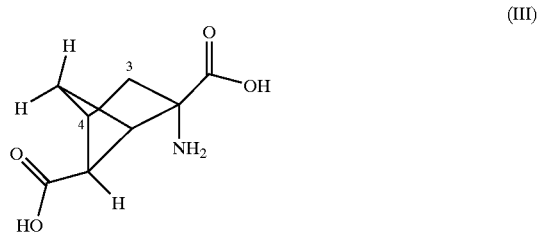

(III)

or a pharmaceutically acceptable salt or prodrug thereof.

Processes for preparing compounds of formula I are provided as further embodiments of the invention and are illustrated by the following procedures in which the meanings of the generic radicals are as given above unless otherwise qualified. A compound of formula I comprising one or more carboxy groups may be prepared from a corresponding compound comprising one or more ($C_1$–$C_6$) alkoxycarbonyl groups, by hydrolysis. Conditions suitable for ester hydrolysis are well known to the art. For example, the hydrolysis may conveniently be carried out under conditions similar to those described in Example 1.

Compounds of formula I may also be prepared using the synthetic methods described in Example 1 hereinbelow, or using the methods or modifications of the methods outlined in Schemes 1 and 2 and in FIGS. 1, 2, 3, 4, 9, 10, and 12–16. The starting materials employed in the synthetic methods described herein are commercially available or are reported in the scientific literature.

Compounds of formula I, where X is oxy, thio, or —N($R_x$)—, can be prepared using the synthetic methods illustrated in FIG. 1. Esterification of the carboxyl group of an intermediate of formula 11 (X=O), 15 (X=NCbz), or 17 (X=S), followed by replacement of the hydroxyl group adjacent to X with a phenylseleno group under acidic conditions yields a compound of formula 18. Oxidation of selenide to selenoxide results in spontaneous elimination (M. Kassou et al., *Tetrahedron Lett.*, 35, 5513 (1994) to yield an allylic alcohol 19, which can be subjected to an amide acetal Claisen rearrangement, to give an amide 20. After saponification of the methyl esters, bromolactonization (I. Shibata et al., *J. Org. Chem.*, 55, 2487 (1990), followed by tin hydride dehalogenation gives β-lactone 22. Closure of the cyclobutane ring using the β-lactone as the alkylating agent is achieved by treatment with a strong base, e.g., LDA, to produce a mixture of stereoisomers 23 and 24 which can be separated. Amide hydrolysis followed by hydrogenolytic removal of the N-benzyl and N-Cbz groups, gives compounds of the invention 25 and 26.

Compounds of formula I wherein X is sulfinyl or sulfonyl can be prepared from corresponding compounds of formula I wherein X is thio, by oxidation, using reagents and techniques which are well known in the art.

Figure 2:
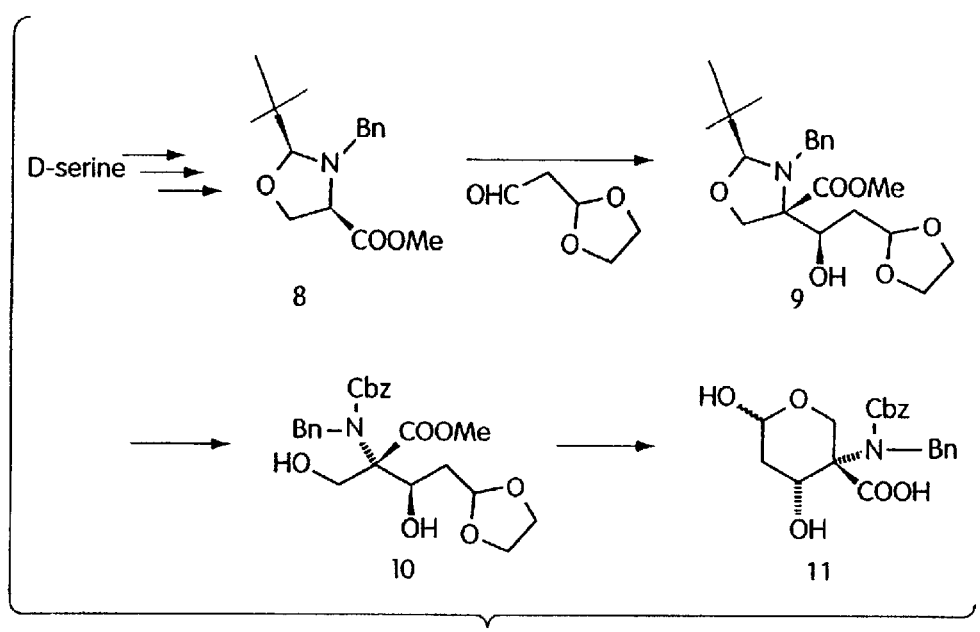
FIG. 2 Illustrates the synthesis of an intermediate of formula 11.

An intermediate useful for preparing a compound of formula I, wherein X is oxy, is the hemiacetal 11. Hemiacetal 11 can be prepared from the oxazolidine 8 (prepared from D-serine in the same way as its enantiomer is prepared from L-serine: E. J. Corey et al., *J. Am. Chem. Soc.*, 114, 10677 (1992) as shown in FIG. 2. Hydroxyalkylation with the monoethylene acetal of malondialdehyde gives an alcohol of formula 9 as the predominant stereoisomer. Acidic removal of the neopentylidene group, followed by protection of the amine as the Cbz derivative gives a diol of formula 10, which can be hydrolyzed with aqueous acid to give hemiacetal 11.

Figure 3:
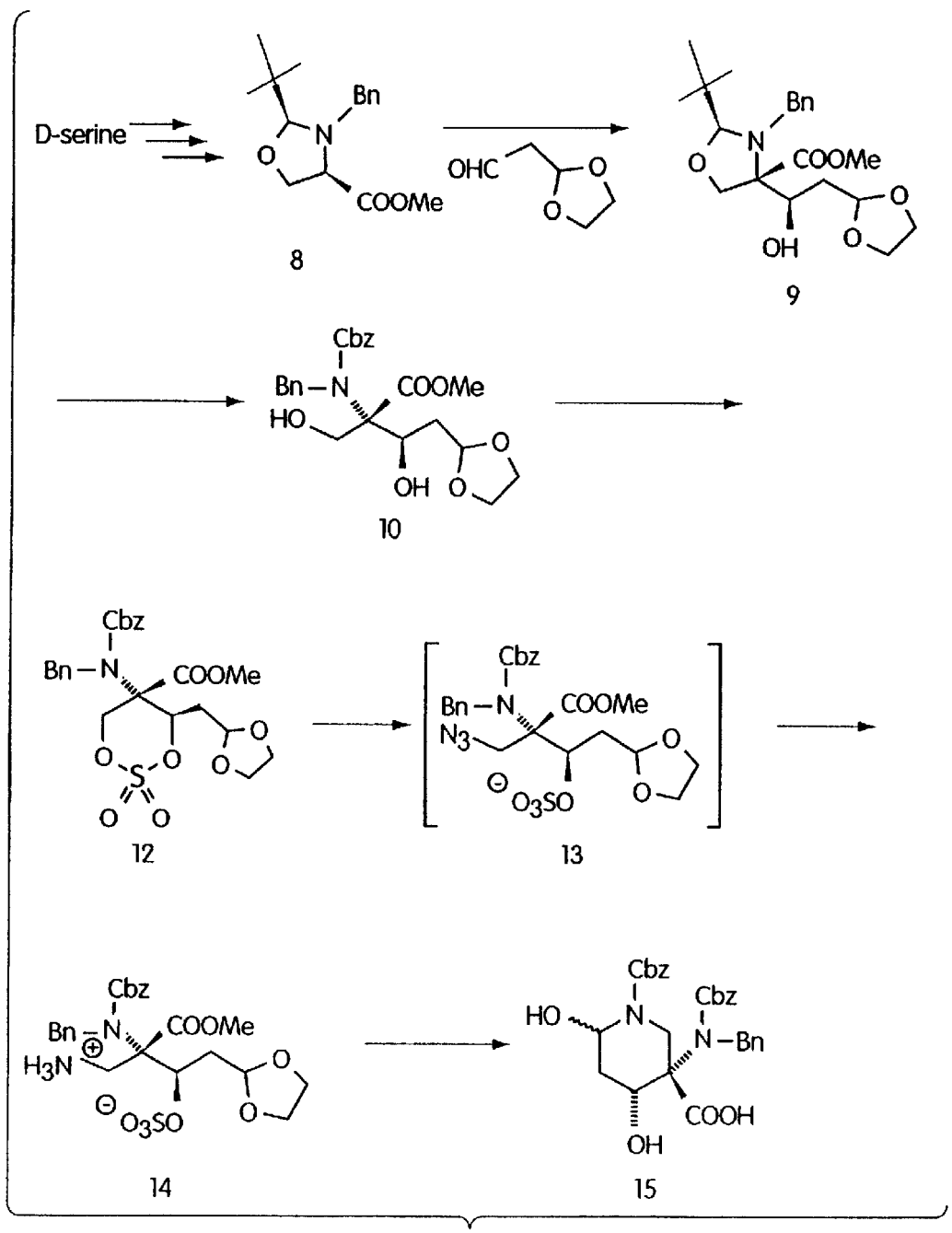
FIG. 3 Illustrates the synthesis of an intermediate of formula 15.

An intermediate useful for preparing a compound of formula I, wherein X is —N($R_x$)— is the hemiaminal 15, which can be prepared as shown in FIG. 3. Formation of the cyclic sulfate 12 from diol 10 followed by nucleophilic displacement with sodium azide, and reduction of the azide to the primary amine gives the acetal 14, which can by hydrolyzed to give hemiaminal 15.

Figure 4:
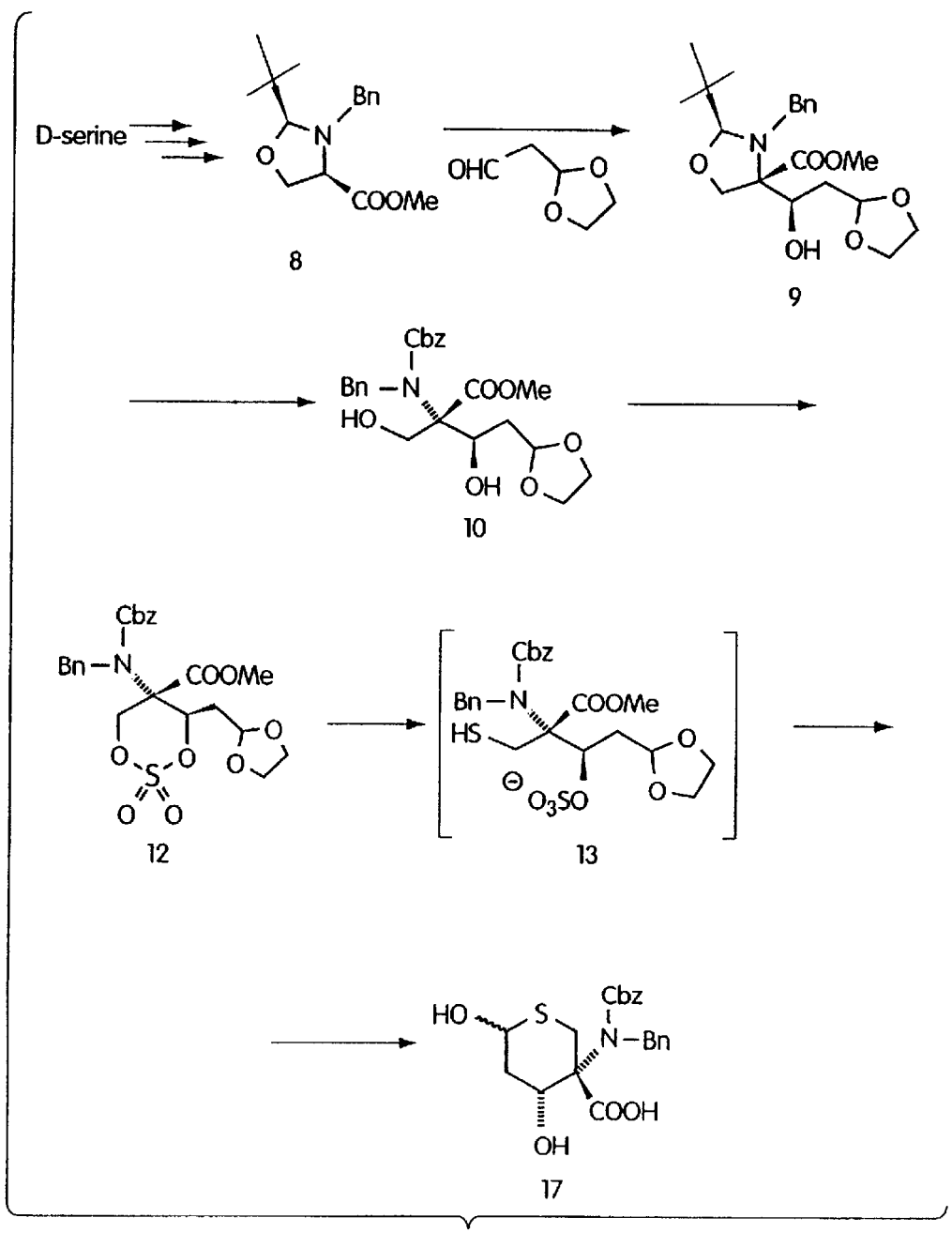
FIG. 4 Illustrates the synthesis of an intermediate of formula 17.
Figure 6:
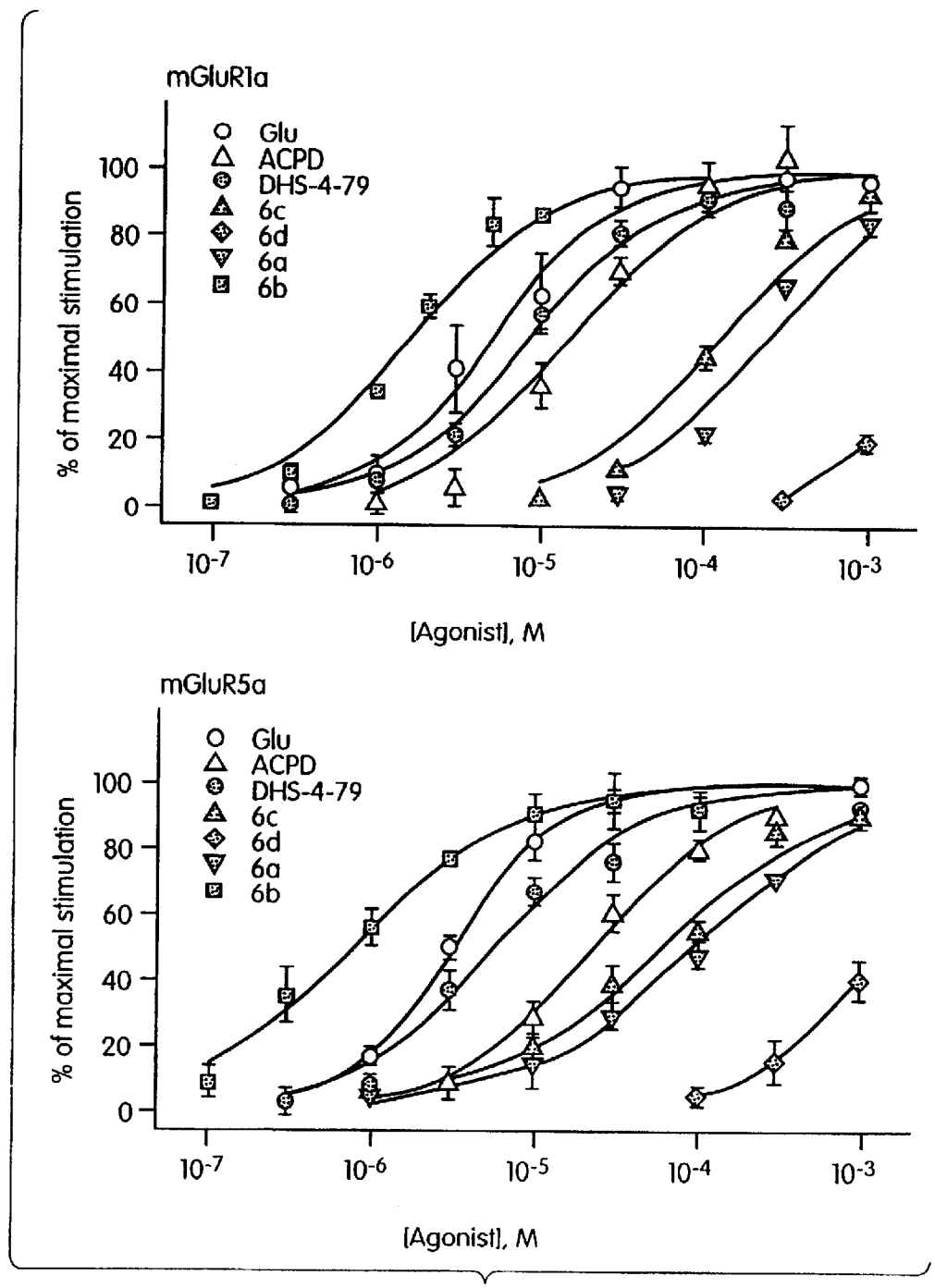
FIG. 6 Shows biological data for compounds of the invention.
Figure 7:
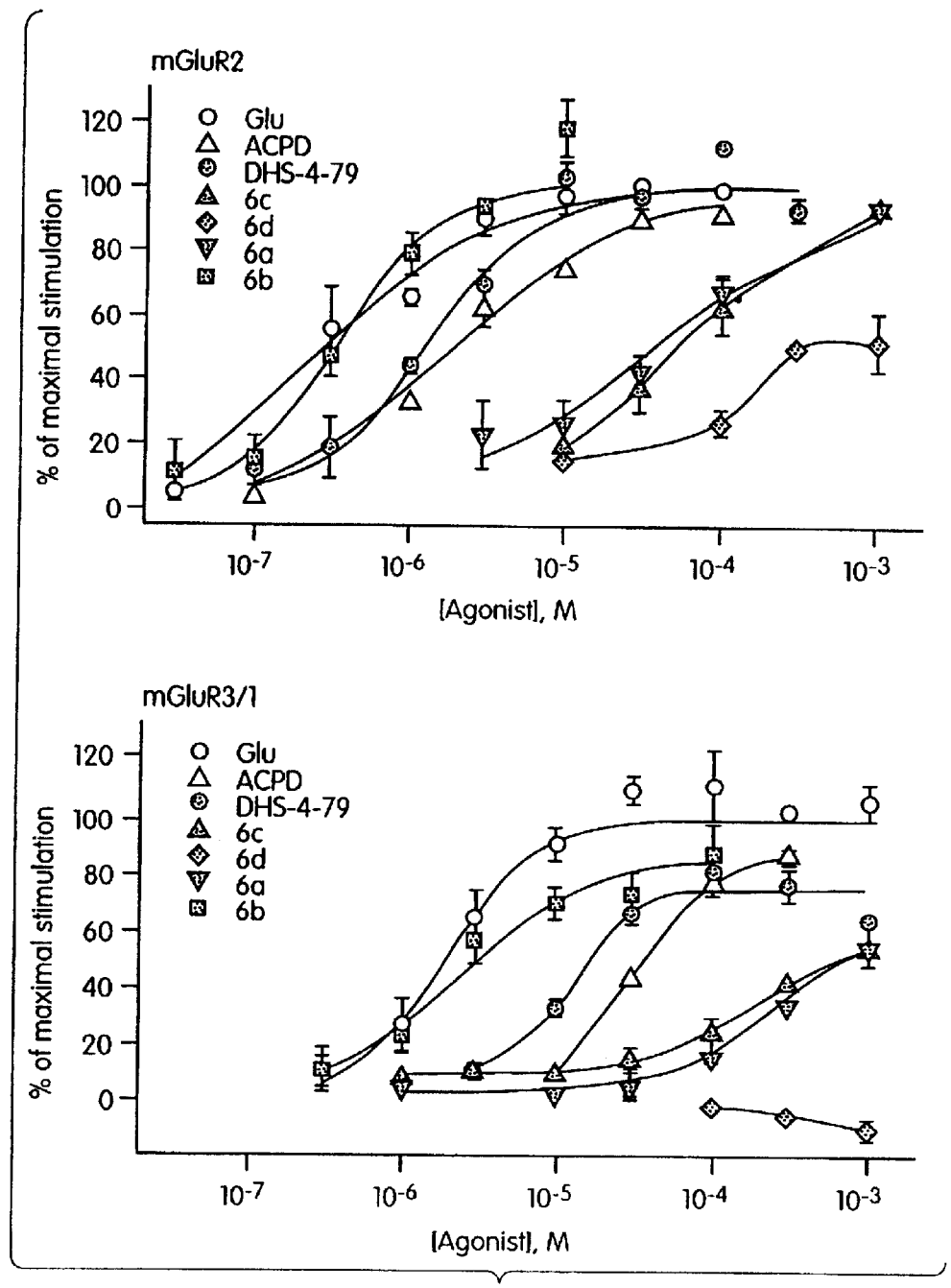
FIG. 7 Shows biological data for compounds of the invention.
Figure 8:
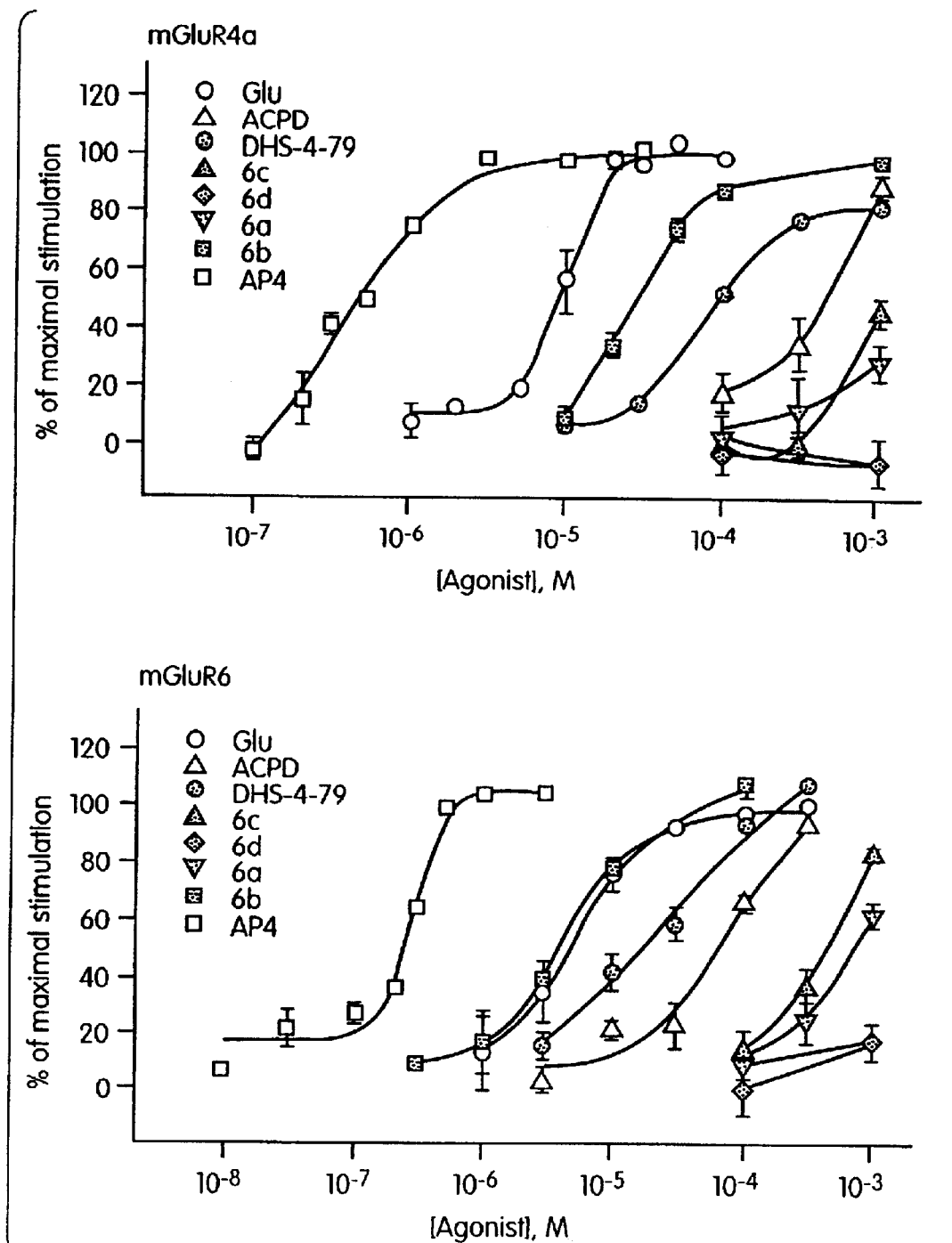
FIG. 8 Shows biological data for compounds of the invention.
Figure 9:
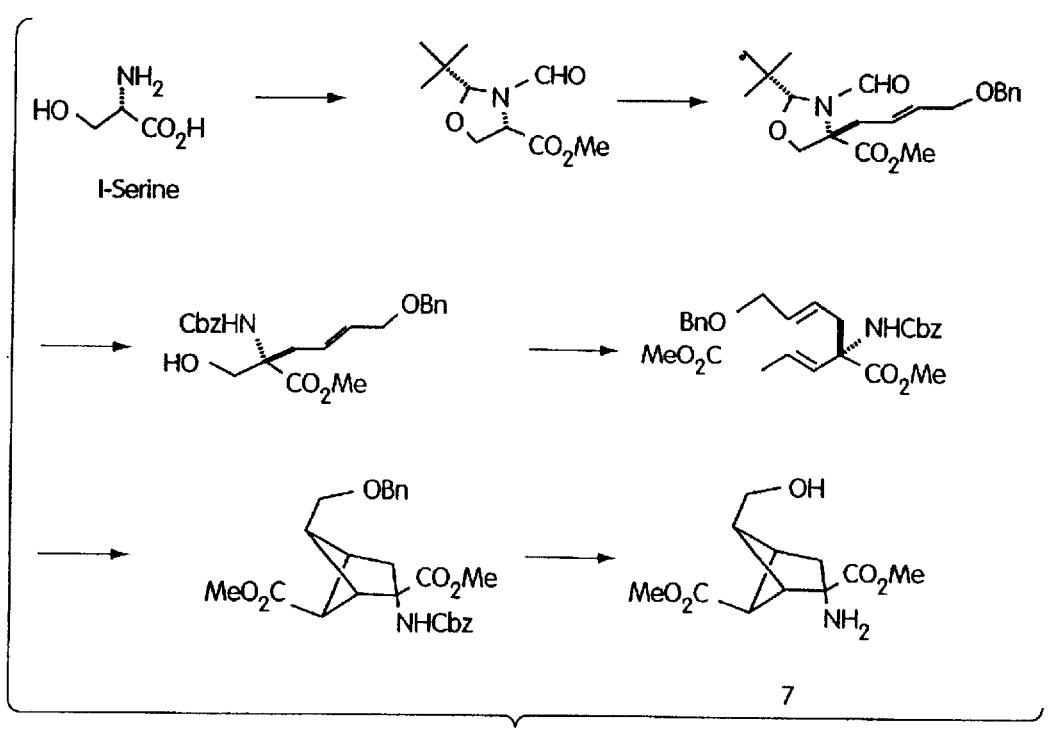
FIG. 9 Illustrates the synthesis of compounds of the invention.
Figure 10:
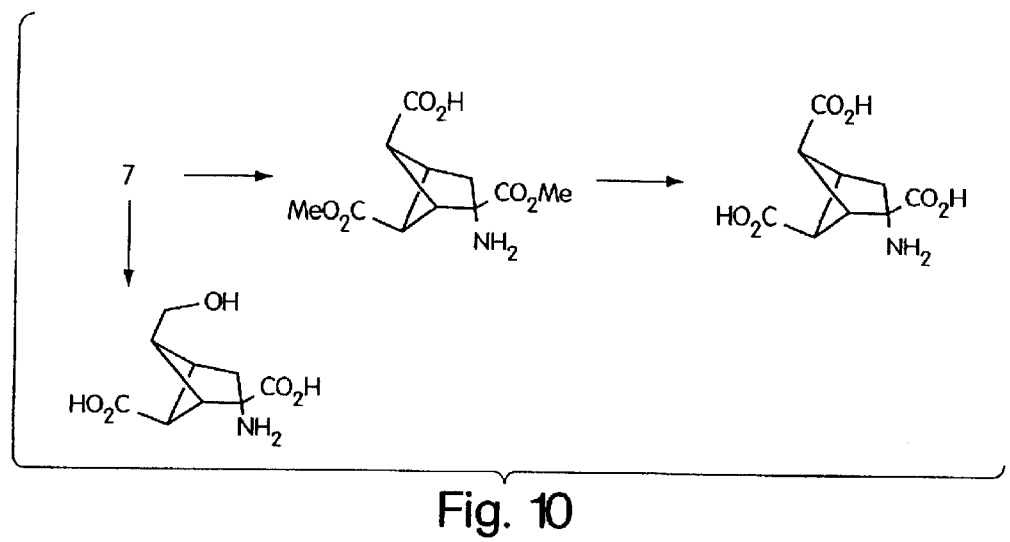
FIG. 10 Illustrates the synthesis of compounds of the invention.
Figure 11:
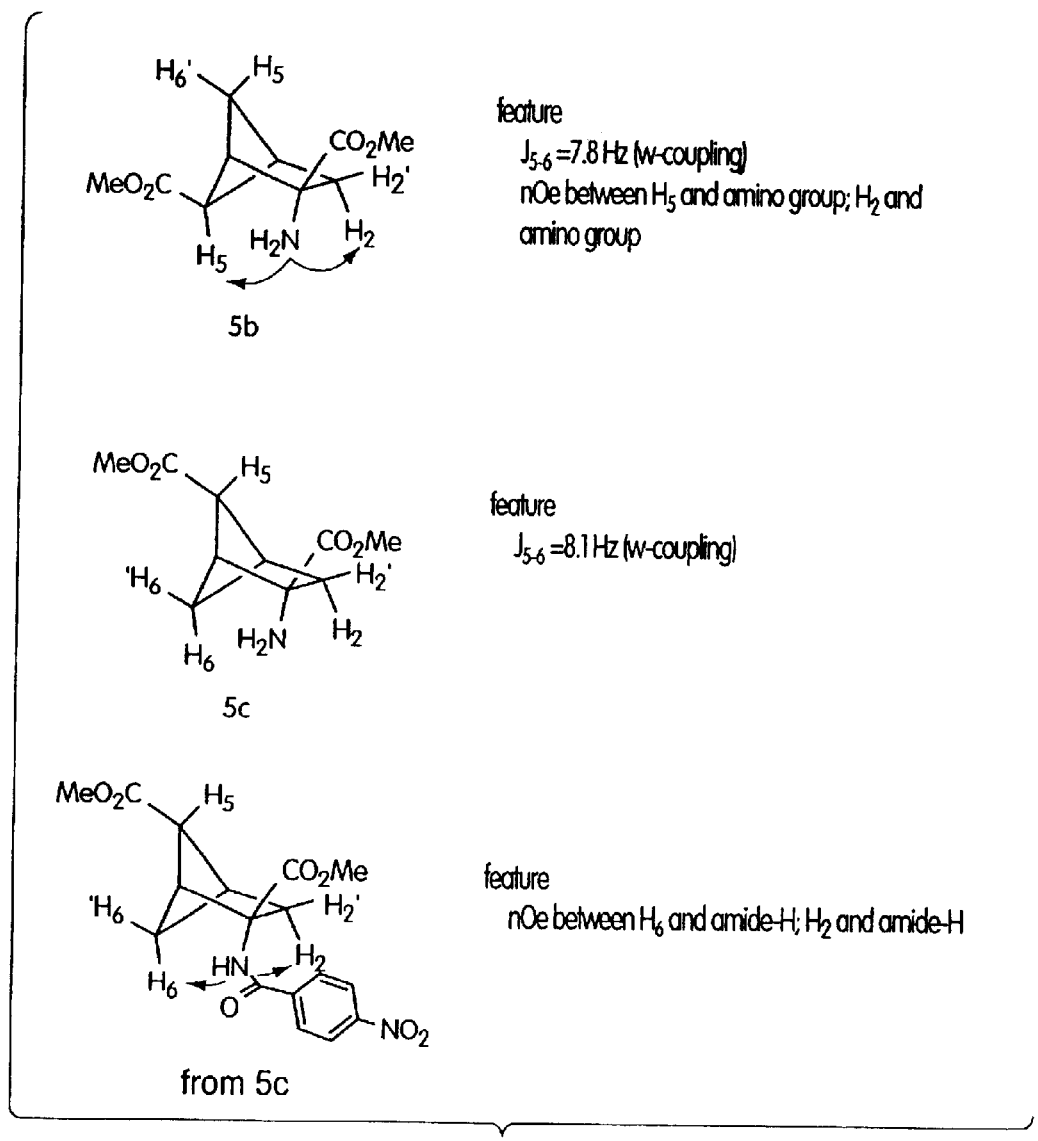
FIG. 11 Shows $^1$H-NMR data for compounds of the invention.

An intermediate useful for preparing a compound of formula I, wherein X is thio is the hemithioacetal 17, which can be prepared as shown in FIG. 4. Formation of the cyclic sulfate 12 from the diol 10, followed by nucleophilic displacement with potassium thioacetate, and deacetylation with methoxide gives the acetal 16, which can be hydrolyzed to give the hemithioacetal 17.

Figure 12:
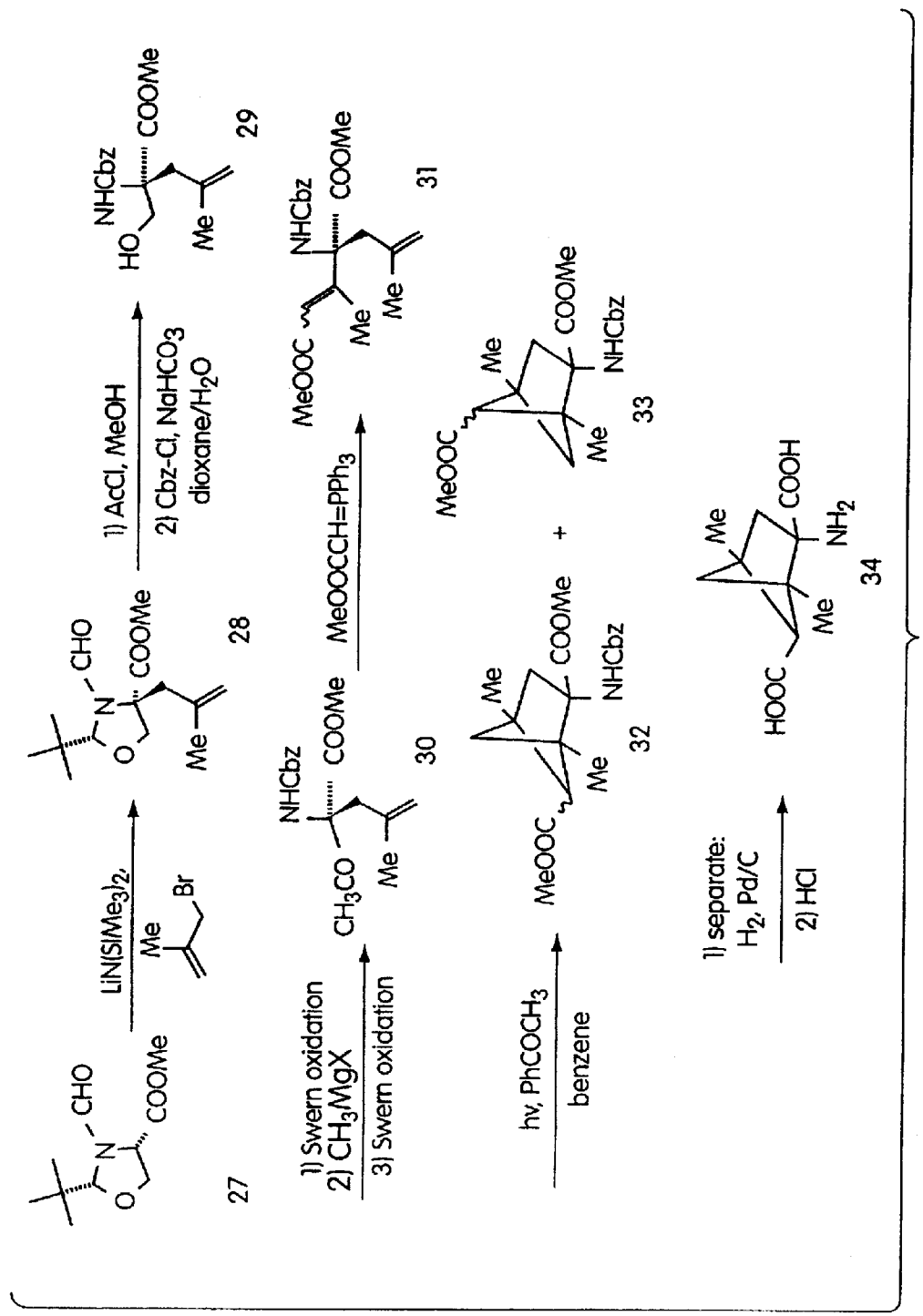
FIG. 12 Illustrates the synthesis of compounds of the invention.
Figure 13:
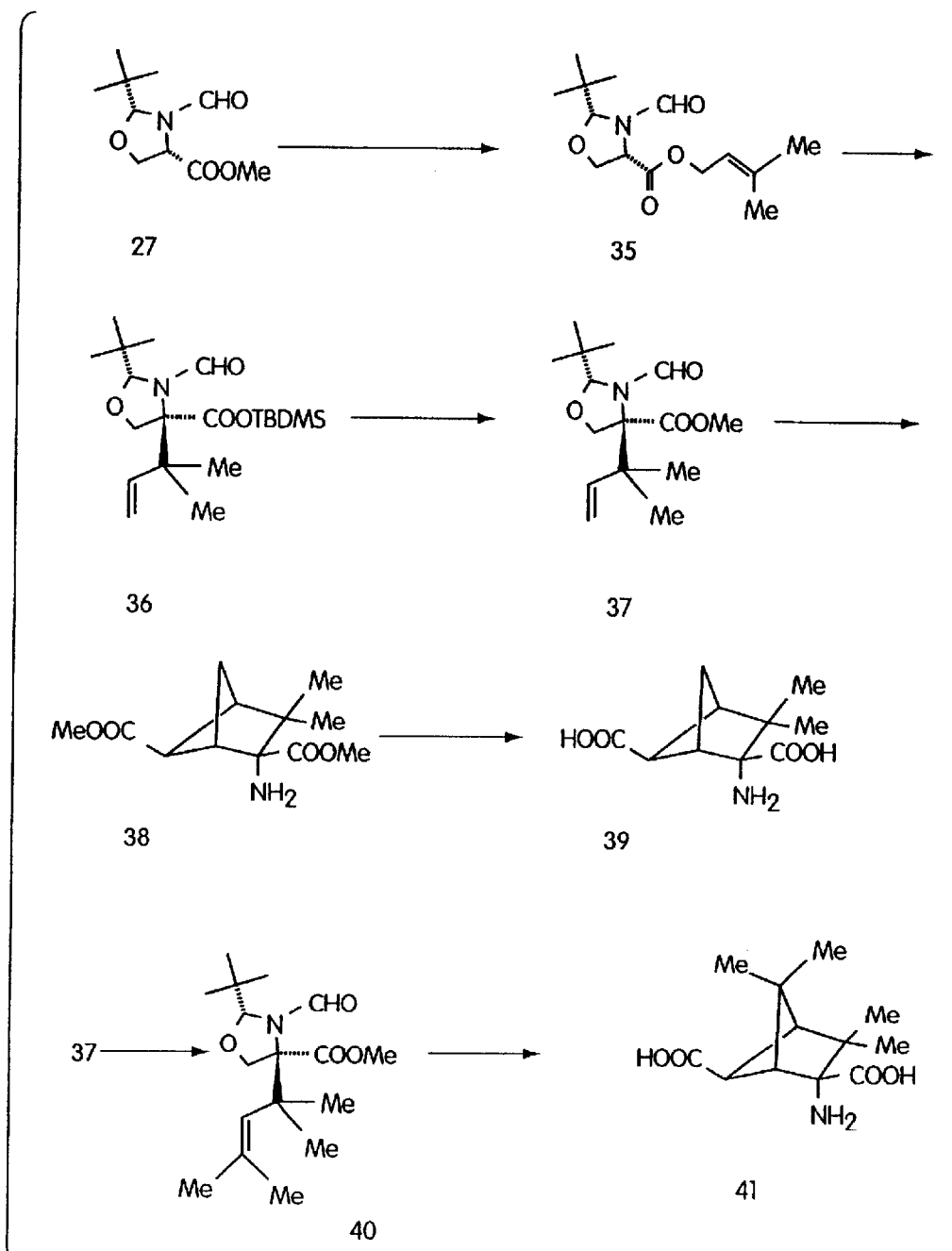
FIG. 13 Illustrates the synthesis of compounds of the invention.

Procedures and intermediates useful for preparing compounds of the invention are also illustrated in FIGS. 12–16. Compound of formula 34, 39, or 41 can be prepared from an aldehyde of formula 27 as illustrated in FIGS. 12 and 13. Alkylation of 27 with methallyl bromide furnishes compound 28, and the second bridgehead methyl group is introduced by Grignard reaction of the aldehyde derived by oxidation of intermediate 29. To achieve dialkylation in position 3, for compounds 39 and 41, α-alkylation of 27 with a tertiary allylic group reacting at its more highly substituted terminus is required. Although such a transformation may be difficult to achieve directly, it can be achieved using an indirect sequence consisting of transesterification using titanium tetraisopropoxide to give compound 35 and Claisen rearrangement to give compound 36. The introduction of substituents in position 6 is achieved by ozonolytic cleavage of the double bond in intermediate 37, followed by Wittig reaction. The compounds 34, 39, and 41, can then be prepared using a sequence analogous to that depicted in Scheme 1.

Figure 14:
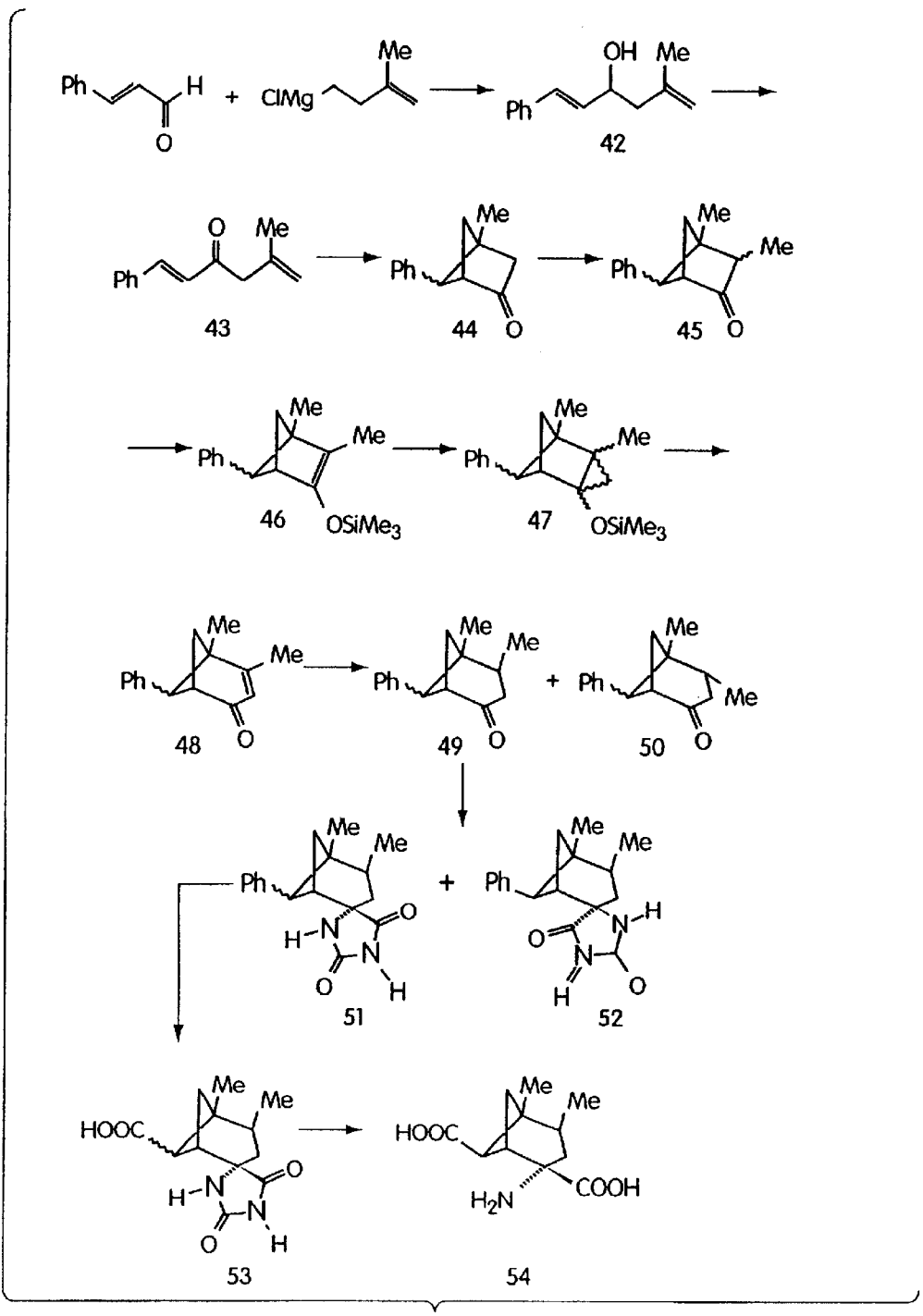
FIG. 14 Illustrates the synthesis of compounds of the invention.
Figure 15:
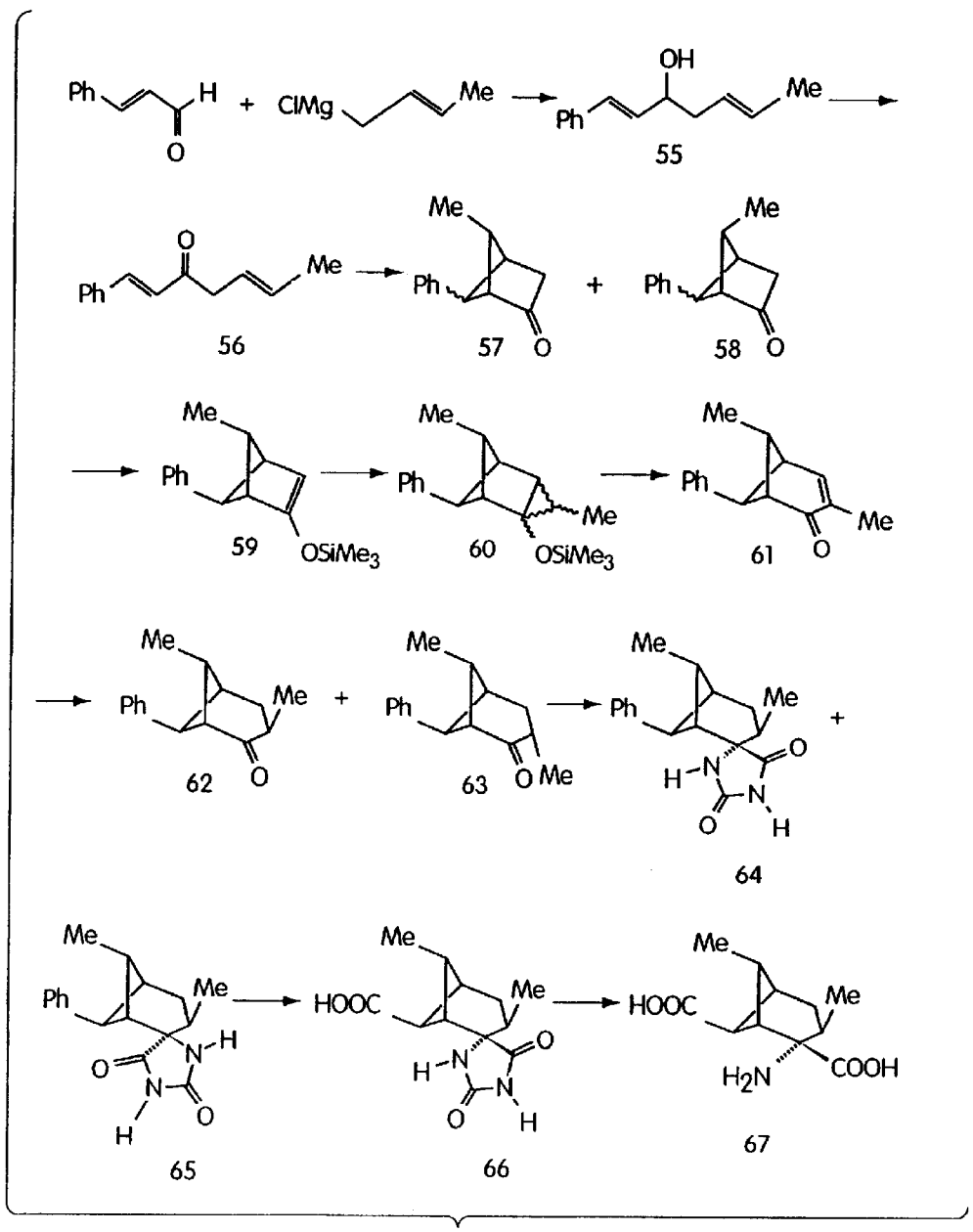
FIG. 15 Illustrates the synthesis of compounds of the invention.

A Compound of formula 54 or 67 can be prepared as illustrated in FIGS. 14 and 15. As photolysis of 1,6-heptadienes leads very predominantly to parallel rather than crossed cycloaddition regiochemistry (i.e., formation of bicyclo[3.2.0]heptanes), the targets have to be accessed instead through ring enlargement of appropriately functionalized bicyclo[2.1.1]hexane precursors. The use of a carbonyl group in position 2 permits 1) the convenient assembly of the photolysis substrates (compounds 43, 56); 2) the execution of a ring enlargement sequence (45 to 48, and 57 to 61) based upon enol silyl ether formation, cyclopropanation, and oxidative cleavage of the resulting silyloxycyclopropane; 3) introduction of an alkyl group into the future position 4 via enolate alkylation (44 to 45); and 4) establishment of the amino acid functionality through a Bucherer-Bergs reaction (49 to 51/52, and 62 to 64/65). The remote carboxyl group in both of these sequences is preferentially introduced in masked form as phenyl, since the starting material cinnamaldehyde is much more accessible than esters of fumaraldehydic acid or maleinaldehydic acid, but those latter two types of compounds can also be used. Phenyl has to be oxidatively degraded to carboxyl, which purpose can be achieved using Sharpless' system consisting of a catalytic amount of a ruthenium compound and sodium metaperiodate as stoichiometric oxidant. In the last step, the hydantoin is hydrolytically cleaved to reveal the free amino acid. Separations of stereoisomers are necessary at various stages because of stereochemical ambiguity both at the carboxyl-bearing carbons as well as at monoalkylated methylene groups. Additionally, the compounds of FIGS. 14 and 15 are obtained in racemic form and may be separated into their enantiomers through techniques, such as HPLC on chiral columns or the formation of diastereomeric derivatives, which can be separated chromatographically or by fractional crystallization and from which the desired amino acids can be recovered hydrolytically. These separation techniques are well known in the art.

Figure 16:
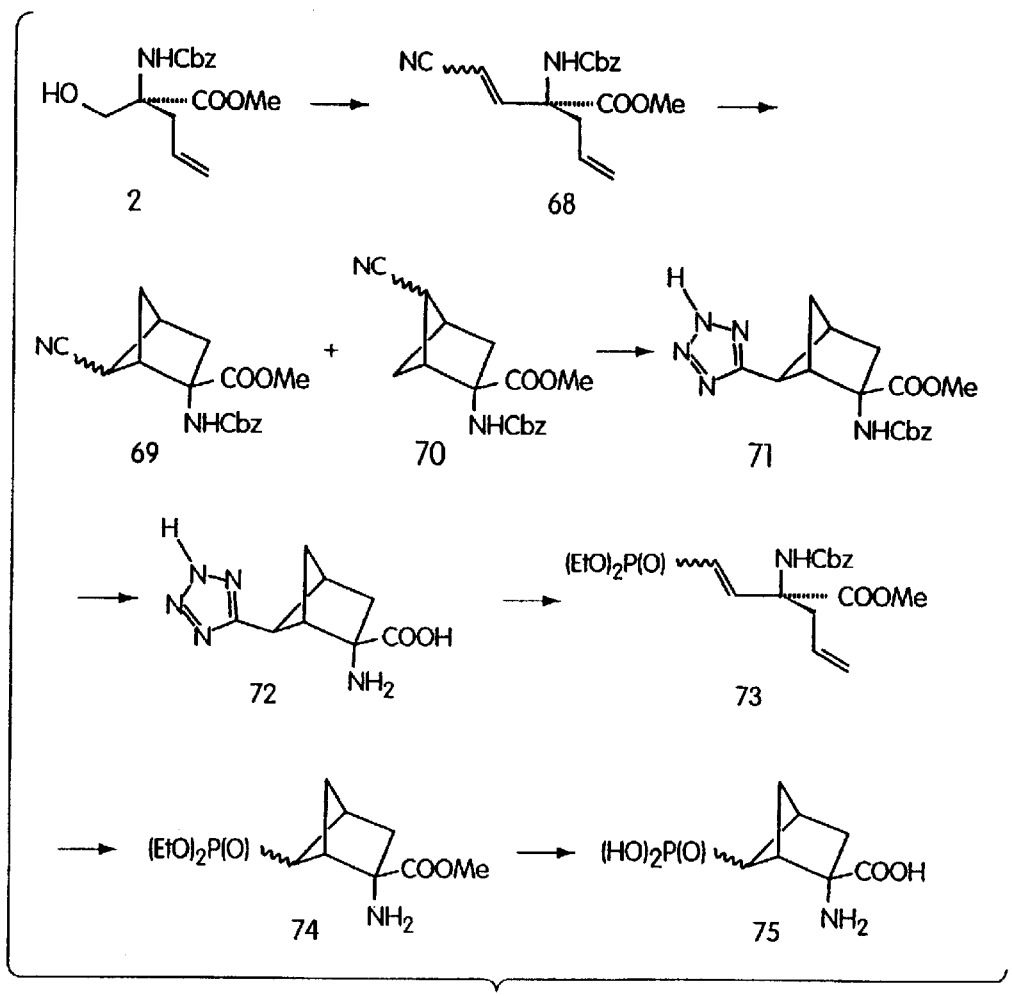
FIG. 16 Illustrates the synthesis of compounds of the invention.

The preparation of tetrazole 72 and phosphonic acid analogue 75 are illustrated in FIG. 16. The general approach is the same as in Scheme 1, but the second methoxycarbonyl group entering the molecule through a Wittig reaction is replaced by cyano (compound 68) or diethoxyphosphoryl (compound 73); in the latter case, the synthetic protocol used is a Wadsworth-Emmons rather than a Wittig reaction. After the photochemical step, the tetrazole is elaborated from the cyano group by reaction with trimethylsilyl azide and trimethylaluminum.

The modifications to the compounds shown in FIGS. 12 through 16 can be implemented singly or in combination with each other; e.g., alkylation in more than one position can be achieved by adjustment of the building blocks used, or the tetrazole analogue of compound 54 can be prepared by transforming the free carboxyl group through routine methods into cyano and applying the procedure of the foregoing paragraph to this intermediate. Furthermore, alkylation is not restricted to methylation but may in an entirely analogous fashion be performed using larger alkyl groups or even functionalized alkyl groups, in which case standard protecting groups are used to temporarily block reactive functionality.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The term "prodrug" is well known in the pharmaceutical arts. As used herein, the term includes compounds that are converted in vivo to a compound of formula I or II, or a salt thereof. The prodrugs of the invention include derivatives that are known in the art to function as prodrugs, e.g., esters of an acid of formula I or II.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

The ability of a compound of the invention to act a modulator (i.e. an agonist, antagonist or partial agonist) of metabotropic glutamate receptors may be determined using pharmacological models which are well known to the art, or using Test A described below. Additionally, the selectivity of a compound of the invention for a specific metabotropic glutamate receptor Group or subtype may also be determined using Test A.

Test A.

Chinese hamster ovary (CHO) cells were used to produce cell lines expressing mGluR1a and mGluR5a (Group 1), mGluR2 (Group II), mGluR6 (Group III) receptors, as well as the chimeric receptor mGluR3/1a which combines the pharmacological properties of mGluR3 (Group II) with the activation of phospholipase C The mGluR4 receptor (Group III) was expressed in baby hamster kidney (BHK) cells.

The activity of new compounds at phospholipase Coupled receptors (mGluR1a, mGluR5a, and mGluR3/1a) was determined by measurement of their ability to increase the hydrolysis of membrane phosphoinositides. CHO cells expressing mGluR1, mGluR5 or mGluR3/1a cultured in 96-well plates were incubated overnight in glutamine-free culture medium supplemented with 0.75 $\mu$Ci myo-[$^3$H] inositol to label the cell membrane phosphoinositides. Before the experiments cells were washed 2 times with 0.5 mL of Locke's solution (156 mM NaCl, 5.6 mM KCl, 3.6 mM NaHCO$_3$, 1 mM MgCl$_2$, 1.3 mM CaCl$_2$, 5.6 mM glucose and 20 mM Hepes, pH 7.4) followed by addition of the same solution with 20 mM LiCl to block the degradation of inositol phosphates. Then receptor ligands were added, and the cells were incubated for 40 minutes at 37° C. The reaction was terminated by aspiration of the medium, and inositol phosphates were extracted for 10 minutes with 0.5 mL of 0.1 M HCl. The separation of [$^3$H]inositol phosphates was performed by anion exchange chromatography. To the collected fractions was added 10 mL of scintillation fluid, and the radioactivity was measured. In each experiment the stimulations induced by the various compounds were normalized to the maximal response induced by 1 mM glutamate and are expressed as per cent of maximal response.

The activity of a compound of the invention at receptors coupled negatively to adenylyl cyclase (mGluR2, mGluR4, mGluR6) was determined by measurements of its ability to decrease the forskolin-induced elevation of cyclic AMP formation. Cells expressing these receptors were cultured on 96-well culture plates. Before experiments, cells were washed three times and preincubated 10 minutes at 37° C. in Locke's medium containing 300 $\mu$M isobutylmethylxanthine to inhibit the activity of phosphodiesterases which degrade cAMP. Then 5 or 10 $\mu$M forskolin was added without or with mGluR agonists, and the incubation was continued for 10 minutes. After the incubation, the medium was rapidly aspirated and cAMP was extracted for 10 minutes with 0.1 M HCl and measured by radioimmunoassay using a magnetic Amerlex RIA kit. Within each experiment the results were normalized to the maximal response induced by 1 mM glutamate for mGluR2 and mGluR4, and by 1 mM 4-aminophosphonobutyrate for mGluR6, and are expressed as per cent of maximal response.

The evaluation of the relative potencies of the tested compounds and the determination of their EC$_{50}$ values was performed by fitting the normalized data to the logistic equation by non-linear regression.

Experimental results from Test A for representative compounds of the invention (prepared as described in Example 1) are shown in FIG. 5. These results demonstrate that compounds of the invention are agonists of metabotropic glutamate receptors. In particular, the representative compounds tested showed selectivity for the Group II receptor mGluR2.

Based on the specific binding of the compounds of the invention to glutamate receptors and their agonist, partial agonist or antagonist activity, the compounds of the invention should have a number of therapeutic uses. For example, an appropriate amount of a compound of formula I can be administered to a subject to prevent or treat (e.g., alleviate the symptoms or slow the progression of) a condition or disorder that is linked (e.g., involves signaling) from metabotropic glutamate receptors, including neurological, neurodegenerative, psychiatric and psychological disorders. Examples of these conditions or diseases include: epilepsy, cerebral deficits subsequent to cardiac bypass surgery and grafting, stroke, cerebral ischemia, pain, spinal cord injury, head trauma, perinatal hypoxia, cardiac arrest and hypoglycemic damage, anxiety and neurodegenerative diseases such as Lou Gehrig's disease (ALS), Huntington's Chorea, AIDS-induced dementia, ocular damage and retinopathy, cognitive disorders, Parkinson's Disease, and Multiple Sclerosis, as well as other conditions that result in progressive loss of neuronal cells and/or cellular function.

The compounds of the invention can also be administered to a subject in order to treat or manage an addiction, e.g., to drugs, including narcotics, cocaine, alcohol, benzodiazepine, nicotine), foods or other substances.

Additionally, compounds of the invention may be useful as pharmacological tools for the further investigation of mGluR function.

For use in therapy or treatment, an effective amount of the compound of formula I, a prodrug thereof, or a pharmaceutical preparation thereof (e.g., a formulation that facilitates passage through the blood brain barrier or that slows down in vivo metabolism) can be administered to a subject in accordance with any method that allows the compound to be taken up by the appropriate organ and perform its intended function. Preferred routes of administration include oral, intravenous and transdermal (e.g., via a patch) administration.

In addition to the above-described therapeutic uses, the compounds of the invention may be labeled (e.g., radioactively using $^3$H, $^{11}$C, $^{14}$C or $^{13}$N, or non-radioactively using $^2$H, $^{13}$C, $^{15}$N or $^{18}$O) and used in research, for example, for studies on receptor function or to elucidate the structure, function or mechanisms of competitive ligand interactions. In addition, labeled compounds can be useful for determining the selectivity, specificity, or potency of novel clinical entities directed at the glutamate receptor. Further, the compounds can be useful for testing competing compounds for the ability to interact with a member of the glutamate receptor family (i.e., in a competitive binding assay).

Generally, compounds of the invention are metabotropic glutamate receptor ligands, i.e., are capable of binding to metabotropic glutamate receptors. As a result, they may demonstrate agonist, antagonist, or partial agonist activity at these receptors. The use of expression cloning techniques has led to the identification of eight mGluR subtypes, which have been placed into three major categories based on their molecular structure, signal transduction mechanisms, and pharmacological properties. Compounds demonstrating agonist, antagonist, or partial agonist activity at Group I, II, or III receptors are useful as described herein, as pharmacological tools or as therapeutic agents. Compounds demonstrating selectivity for one or more receptor sub-types are similarly useful. For therapeutic uses, compounds demonstrating antagonist activity at Group I receptors, or compounds demonstrating agonist or partial agonist activity at Group II or Group III receptors may be preferred.

The invention will now be illustrated by the following non-limiting Examples.

EXAMPLE 1

As illustrated in Scheme 1, oxazolidine 1 was produced using a procedure similar to that described in *Helv. Chim. Acta.* 1987, 70, 1194. Treatment of 1 with HCl in methanol afforded α-allylserine methyl ester which was protected with benzyl chloroformate to give compound 2. The alcohol was oxidized under Swern conditions and the resulting aldehyde treated with methyl (triphenylphosphoranylidene) acetate to produce the α,β-unsaturated ester 3.

Scheme 1

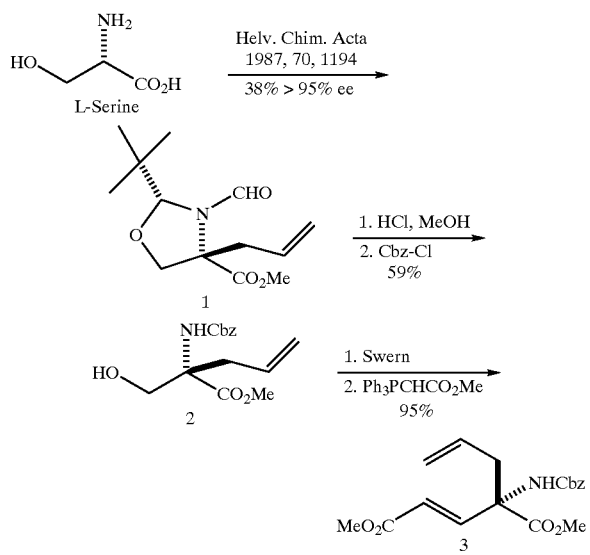

As illustrated in Scheme 2, diene 3 was irradiated in the presence of acetophenone using either a quartz or Pyrex apparatus. Compounds 4 a–c were isolated as a chromatographically homogeneous mixture while 4d was isolated as a single compound (a–d indicates the compound's relative polarity with a being the least polar). The mixture of compounds (4 a–c) was deprotected with Pd/C under all atmosphere of $H_2$ to afford compounds 5 a–c as three separable compounds. Compound 4d was also deprotected using H2 and Pd/C. The diesters 5 a–d, which are also compounds of the invention, were individually treated with 6N HCl at reflux for 1 hour to afford the diacid compounds of the invention 6 a–d.

Scheme 2

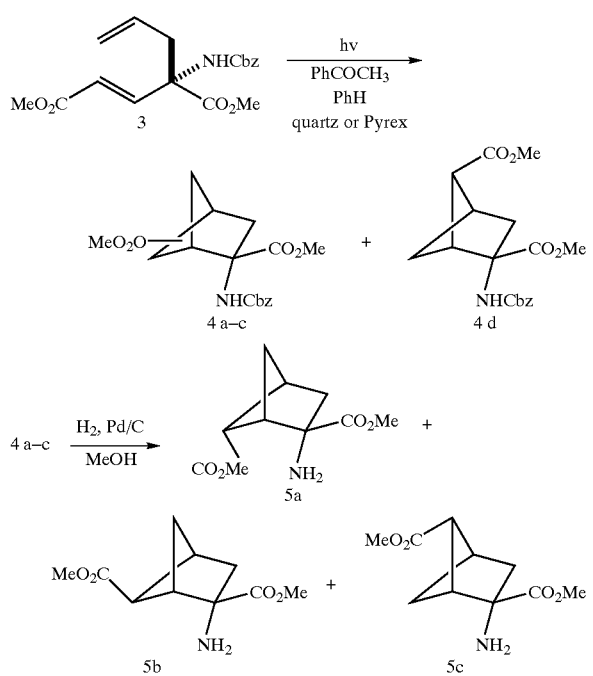

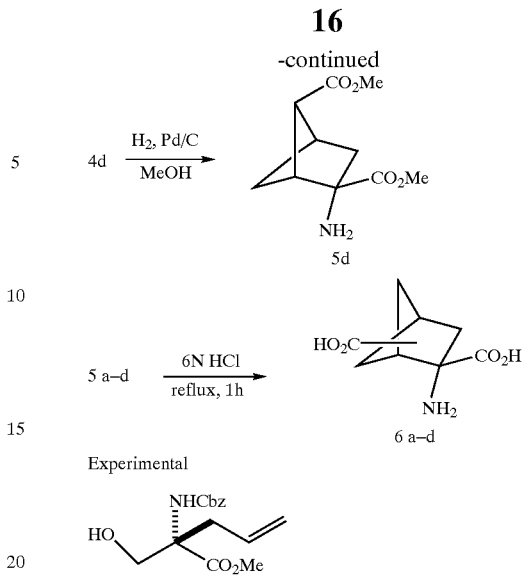

Experimental

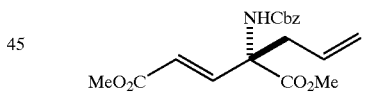

(2S)-2-Allylserine Methyl Ester (2). Acetyl chloride (460 mL, 6470 mmol) was added via addition funnel to methanol (1080 mL) at 0° C. A solution of 1 (18.3 g, 71.8 mmol) in methanol (10 mL) was added and the reaction mixture refluxed for 3 hours. Evaporation of the volatiles in vacuo produced a white solid which was dissolved in dioxane (150 mL) and $H_2O$ (50 mL). $NaHCO_3$ (12.1 g, 144 mmol) and benzyl chloroformate (20.5 mL, 144 mmol) were added, and the reaction mixture was stirred overnight. The reaction mixture was extracted with EtOAc (3×), and the combined organic phases were washed with brine, dried over $MgSO_4$, filtered and concentrated. Column chromatography ($SiO_2$, EtOAc—hexane gradient elution) afforded 2 (12.25 g, 58%) as a colorless oil: $[\alpha]^{RT}_D$ –0.4° (c2.1, $CHCl_3$); $^1H$ NMR (300 MHz, $CDCl_3$) δ7.37–7.29 (m, 5H), 5.79 (br s, 1H), 5.68–5.52 (m, 1H), 5.15–5.01 (m, 4H), 4.18–4.07 (m, 1H), 3.88–3.76 (m, 1H), 3.75 (s, 3H), 3.51 (br s, 1H), 2.78 (dd, J=13.8, 7.8 Hz, 1H), 2.52 (dd, J=14.1, 7.2 Hz, 1H); $^{13}C$ NMR (75 MHz, $CDCl_3$) δ172.25, 155.24, 135.95, 131.02, 128.36, 128.04, 127.90, 119.91, 66.69, 65.08, 64.93, 52.73, 36.73; IR (film) $\nu_{max}$ 3407, 1724 $cm^{-1}$.

Compound 3. A solution of DMSO (0.57 mL, 7.8 mmol) in $CH_2Cl_2$ (8 mL) was added at –78° C. to a solution of oxalyl chloride (0.51 mL, 5.9 mmol) in $CH_2Cl_2$ (4 mL) over 15 minutes. Alcohol 2 (1.15 g, 3.95 mmol) in $CH_2Cl_2$ (20 mL) was added at –78° C. over 10 minutes. After stirring for an additional 10 minutes, $Et_3N$ (2.73 mL, 19.6 mmol) in $CH_2Cl_2$ (15 mL) was added over 10 minutes and the temperature maintained between –60° C. and –70° C. for 30 minutes. The reaction mixture was quenched with a saturated solution of $NH_4Cl$ and extracted with $CH_2Cl_2$ (5×). The combined organic fractions were dried over $MgSO_4$, filtered and concentrated. The residue was dissolved in $CH_2Cl_2$ (45 mL), methyl(triphenylphosphoranylidene) acetate (1.97 g, 5.88 mmol) was added, and the mixture was stirred at RT for 4 h. The reaction mixture was then poured into $H_2O$ and extracted with $CH_2Cl_2$ (5×) The combined organic fractions were dried over $MgSO_4$, filtered and concentrated. Purification of the residue by column chromatography ($SiO_2$, 33% EtOAc—hexane) afforded compound 3 (1.36 g, quant.) as a colorless oil: $[\alpha]^{RT}_D$ −2.2° (c 1.6, CHCl$_3$); $^1$H NMR (300 MHz, CDCl$_3$) δ7.41–7.27 (m, 5H), 7.16 (d, J=15.9 Hz, 1H), 5.98 (d, J=15.9 Hz, 1H), 5.73 (br s, 1H), 5.65–5.50 (m, 1H), 5.20–5.00 (m, 4H), 3.78 (s, 3H), 3.74 (s, 3H), 2.89 (dd, J=13.2, 6.6 Hz, 1H), 2.67 (dd, J=13.5, 7.5 Hz, 1H); $^{13}$C NMR (75 MHz, CDCl$_3$) δ170.80, 166.18, 154.21, 145.33, 136.02, 130.43, 128.47, 128.18, 128.10, 121.47, 120.86, 66.91, 63.20, 53.26, 51.71, 40.26; IR (film) ν$_{max}$ 3352, 1724 cm$^{-1}$.

Compounds 4 a–d. Diene 3 (3.84 g, 11.52 mmol) and acetophenone (0.40 mL) in benzene (400 mL) were first purged with argon and then irradiated with a Hanovia 450 W medium pressure mercury lamp through a Pyrex filter. After 4.5 days, the reaction mixture was evaporated and the residue purified by column chromatography (SiO$_2$, 33% EtOAc—hexanes) to afford a mixture of cis- and trans-3 (R$_f$ 0.8, 50% EtOAc—hexanes, 1.16 g, 30%), 4 a–c (R$_f$ 0.65, 50% EtOAc—hexanes, 1.22 g, 32%) and 4d.

Compound 4d

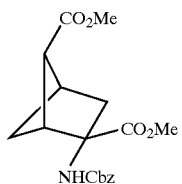

colorless oil; yield 197 mg (5%); R$_f$ 0.53 (EtOAc/hexanes 1/1); $^1$H NMR (CDCl$_3$) δ7.33–7.27 (m, 5H), 5.63 (br s, 1H), 5.06 (br s, 2H), 3,59 (br, s 6H), 3.18 (br s, 1H), 3.04 (d, J=12.3 Hz, 1H), 2.72–2.69 (m, 1H), 1.77 (d, J=12.3 Hz, 1H), 1.53–1.50 (m, 1H), 1.41 (d, J=7.2 Hz, 1H); $^{13}$C NMR (75 MHz, CDCl$_3$) δ172.36 (C), 170.51 (C), 155.22 (C), 136.06 (C), 128.36 (CH), 128.03 (CH), 66.75 (CH$_2$), 63.34 (C), 52.17 (CH$_3$), 51.32 (CH), 51.17 (CH$_3$), 49.61 (CH), 39.81 (CH), 37.08 (CH$_2$), 36.11 (CH$_2$).

Compounds 5 a–c. Compounds 4 a–c (520 mg, 1.50 mmol) and 10% Pd/C (80 mg) were stirred in MeOH (25 mL) under an atmosphere of H$_2$. After 3 hours, the reaction mixture was filtered and concentrated. Silica gel column chromatography (11% MeOH—EtOAc) of the crude mixture gave the compounds 5 a–c.

Compound 5a

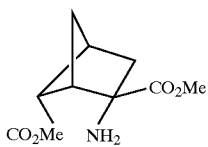

yield 64 mg (20%); R$_f$ 0.80; $^1$H NMR (CDCl$_3$) δ1.07 (d, J=7.5 Hz, 1H), 1.46–1.56 (m, 1H), 1.67 (br s, 2H), 1.97 (dd, J=2.1 and 11.4 Hz, 1H), 2.35 (d, J=11.4 Hz, 1H), 2.61 (s, 1H), 2.64–2.74 (m, 1H), 2.9–3.0 (m, 1H), 3.60 (s, 3H), 3.71 (s, 3H); $^{13}$C NMR (CDCl$_3$) δ36.4, 36.6, 39.7, 49.4, 50.9, 52.0, 52.6, 63.3, 172.4, 176.4.

Compound 5b

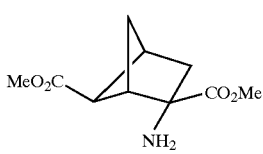

yield 65 mg (20%); R$_f$ 0.6; $^1$H NMR (CDCl$_3$) δ1.29 (t, J=8.1 Hz, H$_6$), 1.54 (dd, J=2.4 and 11.7 Hz, H$_3$), 1.77 (bs, NH$_2$), 2.2–2.3 (m, H$_6$), 2.47 (d, J=11.7 Hz, H$_3$), 2.64–2.74 (m, H$_4$), 2.77 (dd, J=2.7 and 6.9 Hz, H$_1$), 3.01 (d, J=7.8 Hz, H$_5$), 3.73 (s, 3H), 3.74 (s, 3H); $^{13}$C NMR (CDCl$_3$) δ37.6 (C$_6$), 39.9 (C$_3$), 41.6 (C$_4$), 51.6 (Me), 51.7 (Me), 52.1 (C$_1$), 52.8 (C$_5$), 63.3 (C$_2$), 173.7 (CO), 176.1 (CO).

Compond 5c

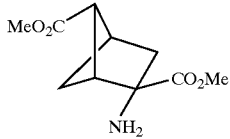

yield 156 mg (49%); R$_f$ 0.49; $^1$H NMR (CD$_3$OD) δ1.54 (dd, J=0.9 and 12.0 Hz, H$_3$), 1.72 (t, J=8.1 Hz, H$_6$), 2.26 (ddd, J=2.7, 5.4 and 8.1 Hz, H$_6$), 2.51 (d, J=8.1 Hz, H$_5$), 2.28–2.38 (m, 1H), 2.5–2.57 (m, H$_4$), 2.72 (dd, J=2.4 and 6.9 Hz, H$_1$), 3.68 (s, 3H), 3.74 (s, 3H), 4.82 (br s, NH$_2$); $^{13}$C NMR (CD$_3$OD) δ36.9 (C$_6$), 41.3 (C$_3$), 42.9 (C$_4$), 52.4 (Me), 53.0 (Me), 54.0 (C$_1$), 55.5 (C$_5$), 64.5 (C$_2$), 172.8 (CO), 175.9 (CO).

Compound 5d

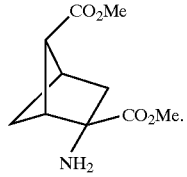

Compound 4d (95 mg, 0.27 mmol) and 10% Pd/C (15 mg) were stirred in MeOH (5 mL) under an atmosphere of H2. After 3 h, the reaction mixture was filtered and concentrated. Purification of the residue by column chromatography (SiO$_2$, 11% MeOH—EtOAc) afforded compound 5d (58 mg, 100%) as a colorless oil. $^1$H NMR (CDCl$_3$) δ1.46 (d, J=11.7 Hz, 1H), 1.5–1.6 (m, 1H), 1.62 (d, J=7.2 Hz, 1H), 1.85 (br s, 2H), 2.63–2.70 (m, 2H), 2.82 (dd, J=1.8 and 11.7 Hz, 1H), 2.87–2.94 (m, 1H), 3.56 (s, 3H), 3.69 (s, 3H).

Compounds 6 a–d. Compound 5 a–d were treated with 6N HCl and stirred at reflux for 1 hour. Evaporation afforded compounds 6 a–d.

Compound 6a

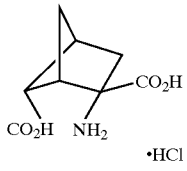

$^1$H NMR (D$_2$O) δ1.50 (d, J=8.1 Hz, 1H), 1.65–1.75 (m, 1H), 2.02 (dd, J=2.7 and 13.2 Hz, 1H), 2.70 (d, J=13.2 Hz, 1H), 2.9–3.0 (m, 1H), 3.06 (bs, 1H), 3.1–3.2 (m, 1H).

Compound 6b

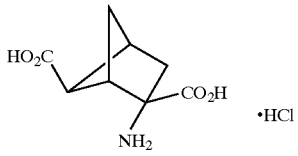

$^1$H NMR (D$_2$O) δ1.86 (t, J=8.7 Hz, 1H), 2.03 (d, J=12.6 Hz, 1H), 2.3–2.4 (m, 1H), 2.63 (d, J=12.6 Hz, 1H), 2.8–3.0 (m, 2H), 3.05–3.02 (m, 1H).

Compound 6c

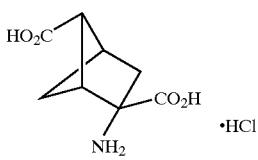

¹H NMR (D₂O) δ1.65 (t, J=9.0 Hz, 1H), 2.01 (d, J=12.6 Hz, 1H), 2.46 (dt, J=2.4 and 9.6 Hz, 1H), 2.63 (br, d J=12.9 Hz, 1H), 2.8–2.9 (m, 1H), 3.08 (dd, J=2.4 and 6.9 Hz, 1H), 3.15 (d, J=8.7 Hz, 1H), Compound 6d

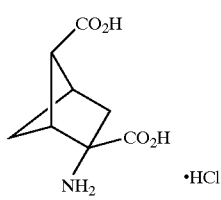

¹H NMR (D₂O) δ1.66 (t, J=9.3 Hz, 1H), 2.02 (d, J=12.6 Hz, 1H), 2.4–2.5 (m, 1H), 2.65 (br d, J=12.9 Hz, 1H), 2.8–2.9 (m, 1H), 3.05–3.15 (m, 1H), 3.18 (d, J=8.7 Hz, 1H).

EXAMPLE 2

The following illustrate representative pharmaceutical dosage forms, containing a compound of formula I, for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii.) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

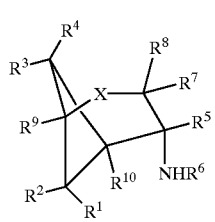

wherein
$R^1$, $R^2$, $R^3$, $R^4$, $R^7$, $R^8$, $R^9$, and $R^{10}$ are each independently hydrogen, carboxy, tetrazolyl, —SO₂OH, —PO(OH)₂, —B(OH)₂, (C₁–C₆)alkyl, (C₃–C₆)cycloalkyl, (C₃–C₆)cycloalkyl(C₁–C₆)alkyl, (C₂–C₆)alkenyl, (C₂–C₆)alkynyl, (C₁–C₆)alkoxy, halo(C₁–C₆)alkyl, hydroxy(C₁–C₆)alkyl, (C₁–C₆)alkanoyl, (C₁–C₆)alkanoyloxy, (C₁–C₆)alkoxycarbonyl, cyano, halo, —CONR$_a$R$_b$, —NR$_c$R$_d$, —SR$_e$, aryl, heteroaryl, aryl(C₁–C₆)alkyl, diaryl(C₁–C₆)alkyl, or heteroaryl(C₁–C₆)alkyl, wherein any aryl or heteroaryl may optionally be substituted with 1, 2 or 3 substituents selected from the group consisting of halo, hydroxy, (C₁–C₆)alkoxy, (C₁–C₆)alkyl, (C₃–C₆)cycloalkyl, (C₃–C₆)cycloalkyl (C₁–C₆)alkyl, (C₁–C₆)alkanoyl, (C₁–C₆)alkanoyloxy, (C₁–C₆)alkoxycarbonyl, cyano, nitro, trifluoromethyl, trifluoromethoxy, and carboxy;

$R^5$ is carboxy, tetrazolyl, (C₁–C₆)alkoxycarbonyl, —SO₂OH, —B(OH)₂, or —PO(OH)₂;

$R^6$ is hydrogen, (C₁–C₆)alkyl, (C₃–C₆)cycloalkyl, (C₃–C₆)cycloalkyl(C₁–C₆)alkyl, aryl, aryl(C₁–C₆) alkyl, heteroaryl, heteroaryl(C₁–C₆)alkyl, (C₁–C₆) alkoxycarbonyl, or (C₁–C₆)alkanoyl;

X is —C($R_f$)($R_g$)—;
each $R_a$, $R_b$ and $R_e$ is independently hydrogen, ($C_1$–$C_6$) alkyl, ($C_3$–$C_6$)cycloalkyl, ($C_2$–$C_6$)alkenyl, ($C_2$–$C_6$) alkynyl, aryl, heteroaryl, benzyl, or phenethyl;
each $R_c$ or $R_d$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;
$R_f$ and $R_g$ are each independently hydrogen, carboxy, ($C_1$–$C_6$)alkyl, ($C_3$–$C_6$)cycloalkyl, ($C_3$–$C_6$)cycloalkyl($C_1$–$C_6$)alkyl, ($C_2$–$C_6$)alkenyl, ($C_2$–$C_6$)alkynyl, ($C_1$–$C_6$)alkoxy, halo($C_1$–$C_6$)alkyl, hydroxy($C_1$–$C_6$)alkyl, ($C_1$–$C_6$)alkanoyl, ($C_1$–$C_6$)alkanoyloxy, ($C_1$–$C_6$)alkoxycarbonyl, cyano, halo, —CONR$_h$R$_i$, —NN$_j$R$_k$, —SR$_m$, aryl, heteroaryl, aryl($C_1$–$C_6$)alkyl, or heteroaryl($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$)alkanoyloxy, ($C_1$$C_6$)alkoxycarbonyl, cyano, nitro, trifluoromethyl, trifluoromethoxy, and carboxy; or $R_f$ and $R_g$ together are oxo (=O) or thioxo (=S);
each $R_h$, $R_i$ and $R_m$ is independently hydrogen, ($C_1$–$C_6$) alkyl, ($C_3$–$C_6$)cycloalkyl, ($C_2$–$C_6$)alkenyl, ($C_2$–$C_6$) alkynyl, aryl, heteroaryl, benzyl, or phenethyl; and
each $R_j$ or $R_k$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_j$ and $R_k$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; or a pharmaceutically acceptable salt or prodrug thereof;
wherein at least one of $R^1$, $R^2$, $R^3$, $R^4$, $R^9$, and $R^{10}$ is carboxy, tetrazolyl, —SO$_2$OH, —PO(OH)$_2$, or —B(OH)$_2$.

2. The compound of claim 1 wherein $R^1$, $R^2$, $R^3$, $R^4$, $R^7$, $R^8$, $R^9$ and $R^{10}$ are each independently hydrogen, carboxy, tetrazolyl, —SO$_2$OH, —PO(OH)$_2$, ($C_1$–$C_6$)alkyl, ($C_3$–$C_6$) cycloalkyl, ($C_3$–$C_6$)cycloalkyl($C_1$–$C_6$)alkyl,($C_1$–$C_6$) alkanoyl, cyano, halo, —NR$_c$R$_d$, aryl, heteroaryl, aryl ($C_1$–$C_6$)alkyl, diaryl($C_1$–$C_6$)alkyl, or heteroaryl($C_1$–$C_6$) alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$) alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$)alkanoyloxy, ($C_1$–$C_6$) alkoxycarbonyl, cyano, nitro, trifluoromethyl, trifluoromethoxy, and carboxy.

3. The compound of claim 1 wherein $R^1$, $R^2$, $R^3$, $R^4$, $R^7$, $R^8$, $R^9$, and $R^{10}$ are each independently hydrogen, carboxy, tetrazolyl, ($C_1$–$C_6$)alkyl, ($C_1$–$C_6$)alkoxy, ($C_1$–$C_6$)alkanoyl, cyano, halo, aryl, or heteroaryl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_1$–$C_6$)alkanoyl, ($C_1$–$C_6$)alkanoyloxy, ($C_1$–$C_6$)alkoxycarbonyl, cyano, nitro, trifluoromethyl, trifluoromethoxy, and carboxy.

4. The compound of claim 1 wherein $R^5$ is carboxy, tetrazolyl, ($C_1$–$C_6$)alkoxycarbonyl, —SO$_2$OH, or —PO(OH)$_2$.

5. The compound of claim 1 wherein $R^5$ is carboxy.

6. The compound of claim 1 wherein $R^6$ is hydrogen, ($C_1$–$C_6$)alkyl, aryl, aryl($C_1$–$C_6$)alkyl, diaryl($C_1$–$C_6$)alkyl, or ($C_1$–$C_6$)alkanoyl.

7. A compound of formula II:

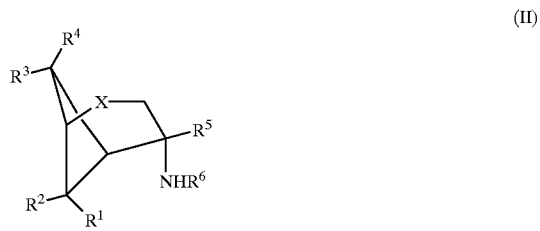

(II)

wherein
$R^1$, $R^2$, $R^3$, and $R^4$, are each independently hydrogen, carboxy, tetrazolyl, —SO$_2$OH, —PO(OH)$_2$, ($C_1$–$C_6$) alkyl, ($C_3$–$C_6$)cycloalkyl, ($C_3$–$C_6$)cycloalkyl($C_1$–$C_6$) alkyl, ($C_2$–$C_6$)alkenyl, ($C_2$–$C_6$)alkynyl, ($C_1$–$C_6$) alkoxy, halo($C_1$–$C_6$)alkyl, hydroxy($C_1$–$C_6$)alkyl, ($C_1$–$C_6$)alkanoyl, ($C_2$–$C_6$)alkanoyloxy, ($C_1$–$C_6$) alkoxycarbonyl, cyano, halo, —CONR$_a$R$_b$, —NR$_c$R$_d$, —SR$_e$, aryl, heteroaryl, aryl($C_1$–$C_6$)alkyl, or heteroaryl ($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$)alkanoyloxy, ($C_1$–$C_6$)alkoxycarbonyl, cyano, nitro, trifluoromethyl, trifluoromethoxy, and carboxy;
$R^5$ is carboxy, tetrazolyl, ($C_1$–$C_6$)alkoxycarbonyl, —SO$_2$OH or —PO(OH)$_2$;
$R^6$ is hydrogen, ($C_1$–$C_6$)alkyl, ($C_3$–$C_6$)cycloalkyl, ($C_3$–$C_6$)cycloalkyl($C_1$–$C_6$)alkyl, phenyl, benzyl, ($C_1$–$C_6$)alkoxycarbonyl, ($C_1$–$C_6$)alkanoyl, or phenethyl;
X is —C($R_f$)($R_g$)—;
each $R_a$, $R_b$ and $R_e$ is independently hydrogen, ($C_1$–$C_6$) alkyl, ($C_3$–$C_6$)cycloalkyl, ($C_2$–$C_6$)alkenyl, ($C_2$–$C_6$) alkynyl, aryl, heteroaryl, benzyl, or phenethyl;
each $R_c$ or $R_d$ is independently hydrogen, ($C_1$–$C_6$)alkyl, ($C_3$–$C_6$)cycloalkyl, ($C_2$–$C_6$)alkenyl, ($C_2$–$C_6$)alkynyl, ($C_1$–$C_6$)alkanoyl, aryl, heteroaryl, benzyl, or phenethyl; or $R_c$ and $R_d$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;
$R_f$ and $R_g$ are each independently hydrogen, carboxy, ($C_1$–$C_6$)alkyl, ($C_3$–$C_6$)cycloalkyl, ($C_3$–$C_6$)cycloalkyl ($C_1$–$C_6$)alkyl, ($C_2$–$C_6$)alkenyl, ($C_2$–$C_6$)alkynyl, ($C_1$–$C_6$)alkoxy, halo($C_1$–$C_6$)alkyl, hydroxy($C_1$–$C_6$) alkyl, ($C_1$–$C_6$)alkanoyl, ($C_2$–$C_6$)alkanoyloxy, ($C_1$–$C_6$) alkoxycarbonyl, cyano, halo, —CONR$_h$R$_i$, —NR$_j$R$_k$, or —SR$_m$, aryl, heteroaryl, aryl($C_1$–$C_6$)alkyl, or heteroaryl($C_1$–$C_6$)alkyl, wherein any aryl or heteroaryl may optionally be substituted with 1, 2 or 3 substituents selected from the group consisting of halo, hydroxy, ($C_1$–$C_6$)alkoxy, ($C_1$–$C_6$)alkyl, ($C_3$–$C_6$)cycloalkyl, ($C_3$–$C_6$)cycloalkyl($C_1$–$C_6$)alkyl, ($C_1$–$C_6$)alkanoyl, ($C_1$–$C_6$)alkanoyloxy, ($C_1$–$C_6$)alkoxycarbonyl, cyano, nitro, trifluoromethyl, trifluoromethoxy, and carboxy; or $R_f$ and $R_g$ together are oxo (=O) or thioxo (=S);
each $R_h$, $R_i$, and $R_m$ is independently hydrogen, ($C_1$–$C_6$) alkyl, ($C_3$–$C_6$)cycloalkyl, ($C_2$–$C_6$)alkenyl, ($C_2$–$C_6$) alkynyl, aryl, heteroaryl, benzyl, or phenethyl; and each $R_j$ or $R_k$ is independently hydrogen, $(C_1-C_6)$alkyl, $(C_3-C_6)$cycloalkyl, $(C_2-C_6)$alkenyl, $(C_2-C_6)$alkynyl, $(C_1-C_6)$alkanoyl, aryl, heteroaryl, benzyl, or phenethyl; or $R_j$ or $R_k$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; or a pharmaceutically acceptable salt thereof;

wherein at least one of $R^1$, $R^2$, $R^3$, and $R^4$ is carboxy, tetrazolyl, or —$SO_2OH$.

8. A pharmaceutical composition comprising a compound of claim 1 in combination with a pharmaceutically acceptable carrier.

9. A therapeutic method for treating a pathological condition or symptom in a mammal which is associated with abnormal activity of a metabotropic glutamate receptor, comprising administering to a mammal in need of such therapy, an effective amount of a compound of claim 1.

10. The method of claim 9 wherein the condition is, or the symptom is associated with epilepsy, cerebral deficits subsequent to cardiac bypass surgery and grafting, stroke, cerebral ischemia, pain, spinal cord injury, head trauma, perinatal hypoxia, cardiac arrest and hypoglycemic damage, anxiety, neurodegenerative diseases, Huntington's Chorea, AIDS-induced dementia, ocular damage, retinopathy, cognitive disorders, Parkinson's Disease, or Multiple Sclerosis.

11. The method of claim 9 wherein the condition results in progressive loss of neuronal cells and/or cellular function.

12. The method of claim 9 wherein the condition is, or the symptom is associated with stroke.

13. The method of claim 9 wherein the condition is, or the symptom is associated with Alzheimer's disease.

14. The method of claim 9, wherein the condition or symptom is associated with morphine dependence.

15. A therapeutic method for preventing a pathological condition or symptom in a mammal which is caused soley by abnormal activity of a metabotropic glutamate receptor, comprising administering to a mammal in need of such therapy, an effective amount of a compound of claim 1.

* * * * *